(12) United States Patent
Torvinen et al.

(10) Patent No.: US 10,269,174 B2
(45) Date of Patent: Apr. 23, 2019

(54) MANUFACTURING A CUSTOMIZED SPORT APPAREL BASED ON SENSOR DATA

(71) Applicant: adidas AG, Herzogenaurach (DE)

(72) Inventors: Vesa-Pekka Torvinen, Weisendorf (DE); Michael Welker, Fürth (DE); Christian Lott, Kaiserslautern (DE); Gerd Rainer Manz, Erlangen (DE); Alain Andre Walter, Herzogenaurach (DE); Burkhard Dümler, Erlangen (DE)

(73) Assignee: adidas AG, Herzogenaurach (DE)

(*) Notice: Subject to any disclaimer, the term of this patent is extended or adjusted under 35 U.S.C. 154(b) by 0 days.

(21) Appl. No.: 15/416,185

(22) Filed: Jan. 26, 2017

(65) Prior Publication Data

US 2017/0213382 A1 Jul. 27, 2017

(30) Foreign Application Priority Data

Jan. 27, 2016 (DE) .................. 10 2016 201 151

(51) Int. Cl.
*G06T 17/00* (2006.01)
*A43B 3/00* (2006.01)
*A43B 5/00* (2006.01)
*A43D 1/02* (2006.01)
*A43B 13/18* (2006.01)
(Continued)

(52) U.S. Cl.
CPC ............ *G06T 17/00* (2013.01); *A43B 3/0005* (2013.01); *A43B 5/00* (2013.01); *A43B 13/181* (2013.01); *A43B 23/0245* (2013.01); *A43D 1/02* (2013.01); *A63B 24/0062* (2013.01); *A43D 2200/60* (2013.01); *A63B 2220/20* (2013.01); *A63B 2220/30* (2013.01); *A63B 2220/40* (2013.01); *A63B 2220/56* (2013.01);
(Continued)

(58) Field of Classification Search
None
See application file for complete search history.

(56) References Cited

U.S. PATENT DOCUMENTS

| 2014/0182170 A1* | 7/2014 | Wawrousek | A43B 7/14 36/103 |
| 2015/0324751 A1* | 11/2015 | Orenstein | G06F 19/3481 702/3 |

(Continued)

FOREIGN PATENT DOCUMENTS

| JP | 2016-501114 A | 1/2016 |
| WO | WO2014/100462 | 6/2014 |

OTHER PUBLICATIONS

Fulk, George D., et al. "Identifying activity levels and steps in people with stroke using a novel shoe-based sensor." Journal of Neurologic Physical Therapy 36.2 (2012): 100.*

(Continued)

*Primary Examiner* — Ryan M Gray
(74) *Attorney, Agent, or Firm* — Sterne, Kessler, Goldstein & Fox P.L.L.C.

(57) ABSTRACT

An article of sports apparel being customized for a person is provided, and may be manufactured based on a digital model, the digital model built based on received sensor data, the received sensor data obtained by at least one sensor integrated into another article of sports apparel, and the sensor data is obtained while the other article of sports apparel is worn by the person during a sports activity.

23 Claims, 14 Drawing Sheets

Figure 1:
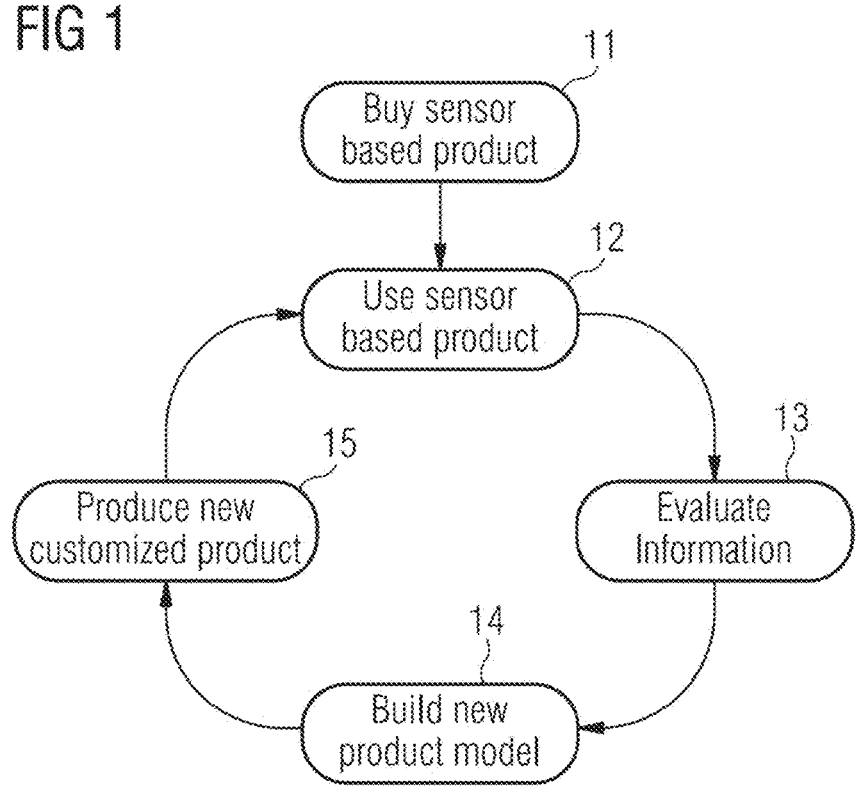

(51) Int. Cl.
*A43B 23/02* (2006.01)
*A63B 24/00* (2006.01)
(52) U.S. Cl.
CPC ..... *A63B 2220/62* (2013.01); *A63B 2220/833* (2013.01); *A63B 2230/06* (2013.01); *A63B 2230/50* (2013.01)

(56) References Cited

U.S. PATENT DOCUMENTS

| | | | | |
|---|---|---|---|---|
| 2015/0351493 | A1 | 12/2015 | Ashcroft | |
| 2016/0088090 | A1* | 3/2016 | Durham | H04W 4/006 709/201 |
| 2017/0065022 | A1* | 3/2017 | Smith | A43D 1/02 |
| 2017/0068774 | A1* | 3/2017 | Cluckers | A61B 5/743 |
| 2017/0187669 | A1* | 6/2017 | Do | H04L 51/32 |

OTHER PUBLICATIONS

European Search Report directed to European Patent Application No. EP I7 15 3277.3-1655, dated Jun. 20, 2017; 9 pages.

\* cited by examiner

RUNNING STYLE

Heel striker

15° angle

GROUND CONTACT TIME

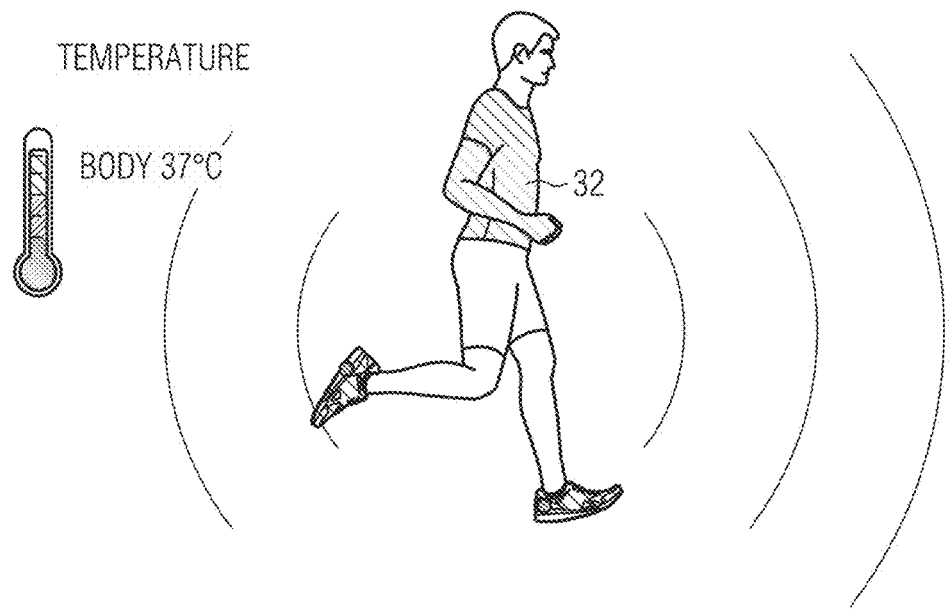

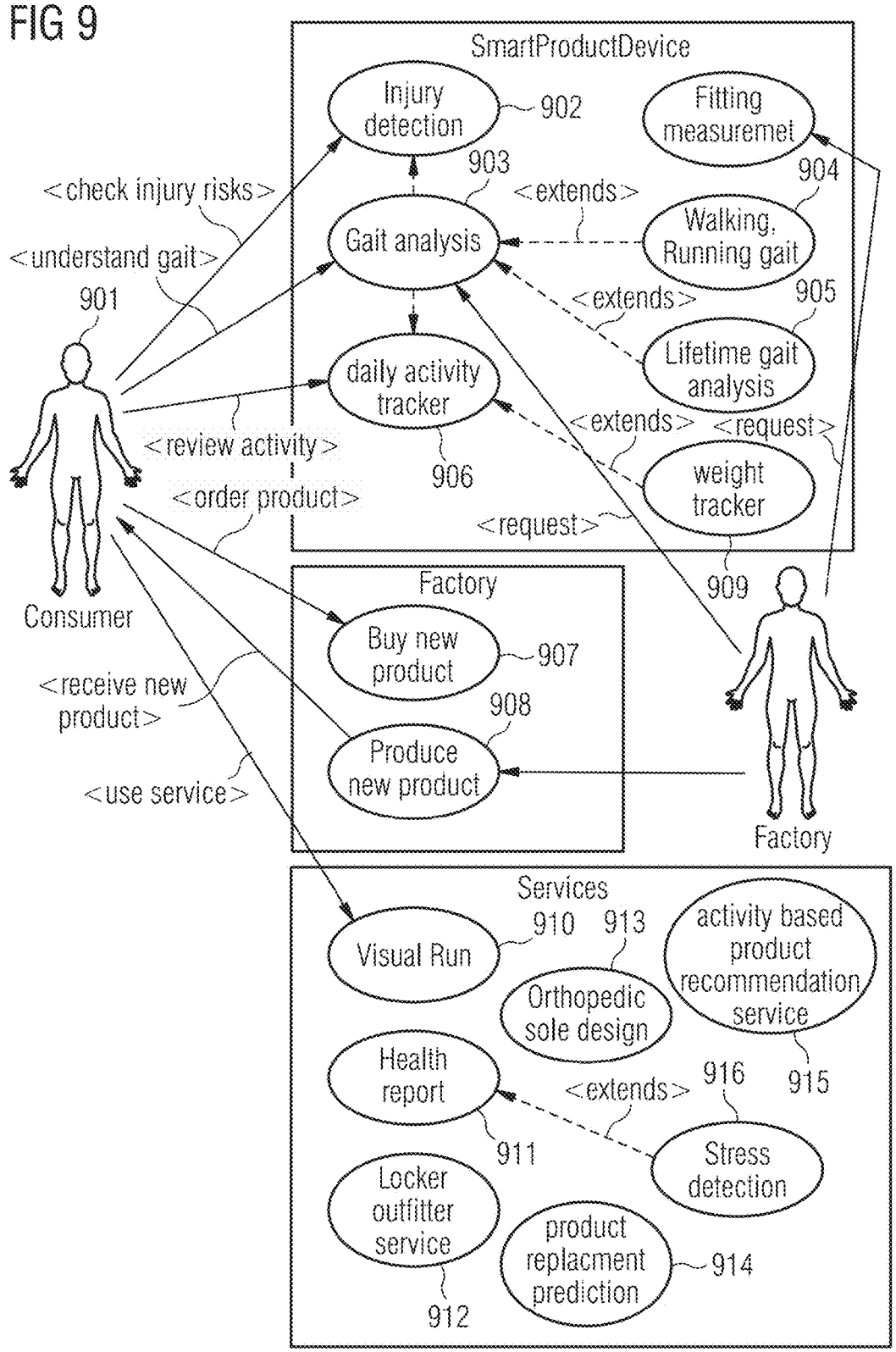

MANUFACTURING A CUSTOMIZED SPORT APPAREL BASED ON SENSOR DATA

FIELD OF THE INVENTION

The present invention relates to an article of sports apparel being customized for a person and to a method of manufacturing such an article of sports apparel.

BACKGROUND OF THE INVENTION

Articles of sports apparel like shirts, jerseys, pants and shoes are usually manufactured as ready-made, mass-produced finished products. They are usually not custom tailored according to measurements, but rather generalized according to anthropometric studies. Thus, sports shirts for example are available in certain fixed sizes like for example "L" (large), "M" (medium) and "S" (small), wherein a differentiation in size and cut is often made between shirts for men and women. Likewise, sports shoes are available in fixed sizes too. For example, according to the continental European system used in France, Germany, Spain and most other continental countries, the shoe size in so-called Paris points is 3/2 of the last length in centimeters. Additionally, a differentiation is sometimes made between different shoe widths.

In the area of professional and ambitious amateur sports, it is known to customize sports apparel up to a certain point. Such customization is often done based on a static analysis, e.g., length and size measurements of the athlete's body. Based on those measurements, customized sports apparel, for example a soccer shoe is then manufactured.

Dynamic analyses, while being rare, are known as well. To this end, the athlete is equipped with one or more sensors which are, e.g., attached to one or more of the athlete's limbs and engages in a typical athletic activity. The gathered sensor data is then processed and used to manufacture customized sports apparel. Alternatively, a video analysis of the athlete engaging in the athletic activity is made. To this end, a video of the athlete is recorded and analyzed. Based on this analysis, a customized sports apparel is then manufactured. For example, a runner may be filmed while running on a treadmill. An orthopedically trained person may then extract information (e.g. supination and pronation) from the filmed video which is then used for manufacturing a customized running shoe.

However, the mentioned techniques for customizing sports apparel have several disadvantages. They are rather expensive as additional equipment like special sensors, video cameras, treadmills, etc. are needed. Furthermore, these techniques require personnel trained in sports medicine and/or orthopedics. More-over, as such analyses are usually performed during a limited amount of time, they do not show long-term evolution of the athlete's performance characteristic and are prone to day-to-day variations in such performance characteristics. Furthermore, as they are performed in a laboratory-like environment, such analyses do not provide any context information, i.e. information about the environment in which the athlete typically performs sports activities.

BRIEF SUMMARY OF THE INVENTION

Therefore, it is the objective of the present invention to overcome the above-mentioned disadvantages of the prior art, e.g., to provide a sports apparel which is customized for a person at moderate additional manufacturing costs taking into account long-term variations in the person's performance characteristics and information about the environment in which the person typically performs his/her sports activities.

This objective is met by a sports apparel being customized for a person, wherein the sports apparel is manufactured based on a digital model, wherein the digital model is build based on received sensor data, wherein the received sensor data is obtained by at least one sensor integrated into another sports apparel, and wherein the sensor data is obtained while the other sports apparel is worn by the person during a sports activity.

The sports apparel according to the invention is manufactured based on a digital model. This allows the sports apparel to be manufactured by fully automated production techniques including 3D printing, placement of components by robots, knitting machines, etc. Such techniques are able to produce customized sports apparel at moderate costs and high throughput. Furthermore, it is possible to manufacture sports apparel not only in a factory, but also e.g. in a store.

The digital model according to the present invention can be a three-dimensional model of the apparel including a functional description. The functional description can include information such as which materials are used, where materials (e.g. patches) are placed, which sensors are used and where sensors are placed.

As the digital model is built based on received sensor data, it is possible to consider the individual anatomy and/or biodynamical properties of a person. Rather than conventional mass-production techniques which rely on statistical data of a representative population average, the sensor data based digital model of the present invention allows to consider individual deviations from such an average and characteristics specific for the person for which the customized sports apparel is to be manufactured.

As the received sensor data is obtained by at least one sensor integrated into another sports apparel, and wherein the sensor data is obtained while the other sports apparel is worn by the person during a sports activity, the sensor data and the derived digital model are not only specific for the person, but also for how he/she performs in his/her natural environment (for example as opposed to the laboratory conditions of other systems).

Thus, the digital model and the derived sports apparel may reflect the conditions under which the person typically performs a sports activity. For example the at least one sensor (for example an accelerometer) may be integrated into a running shoe and the sensor data may reflect that the person runs on hard asphalt tracks most of the time. Accordingly, the digital model for a new customized running shoe would consider that a midsole with good cushioning characteristics would be needed.

In the context of the present invention, the sports apparel may be any type of apparel including caps, t-shirts, pants, jerseys, shoes, socks, etc. Socks, for example may comprise embedded sensors (such as temperature sensors, capacitive sensors, piezo sensors and the like). Socks have direct skin contact which is advantageous when measuring for example the body temperature, heart rate, skin conductivity and the like. Thus, sensors integrated into socks may deliver rather accurate sensor data. Furthermore, socks are rather cheap to manufacture.

The sports apparel in the context of the present invention may comprise a built-in heart rate monitor. The heart rate could be transmitted continuously to a receiver, e.g. in a smartphone, smartwatch, tablet computer or the like. Such a sports apparel could replace the traditional wrist or breast belt devices used to measure heart rate. The sports apparel in the context of the present invention could be capable of measuring the UV light impact. If such UV light impact crosses a certain threshold, the user may obtain a feedback and may be prompted to get out of the sunlight. Such feedback may be provided on a smartwatch, smartphone, tablet computer or may be provided by an acoustic and/or optical indicator arranged on the apparel.

In the context of the present invention, a "receiver" is understood as comprising a transceiver (i.e. a combination of transmitter and receiver) as well.

The sports apparel in the context of the present invention could also be equipped with a gas sensor. Such a sensor may provide information about the composition of gas produced by the user's body. Thus, a smell indication may be provided to the user and he or she may be recommended to take a shower or to change the apparel. The sports apparel in the context of the present invention may also be equipped with a respiration sensor to detect the respiration rate of the user.

Another example is an accelerometer and/or a gyroscope integrated into a running shoe. Based on the sensor data obtained from these sensors, the running style of the person may be detected and feedback may be given to the person. The feedback may recommend to the person to change his/her running style to prevent injuries or to train more efficient.

The sensor data may include at least one parameter of the group comprising distance, speed, pace, heart rate, body temperature, weight, blood flow, energy expenditure and geographic position. These parameters are suitable to provide important information about the person, his/her anatomy and/or biodynamics and the environment in which he/she typically performs athletic activities.

The at least one sensor may be one of a gyroscope, accelerometer, magnetometer, temperature sensor, pressure sensor, bending sensor, piezo element, step counter, moisture sensor and positioning system (like for example GPS, GLONASS or Galileo). Such types of sensors are able to provide important information about the person, his/her anatomy and/or biodynamics and the environment in which he/she typically performs athletic activities.

The sensor data may comprise sensor data from an accelerometer and/or a gyroscope. These types of devices deliver information about the biodynamical aspects of the person's activity. If the sensor is e.g. integrated in a running shoe, it is possible to extract information about the person's gait cycle and to customize a running shoe based on this information. Also, if the person typically runs in more hilly ground, this is reflected in the sensor data and the digital model. The outsole of the customized running shoe may then be provided with more traction to account for slopes.

The sports apparel and the other sports apparel may be a shoe. In particular, the sports apparel and the other sports apparel may be a sports shoe. The invention is in particular advantageous for sports shoes because wearing a proper shoe is important from an orthopedic point of view. Furthermore, the potential for performance improvements by wearing customized shoes is rather high compared to not customized shoes.

A shoe in the context of the present invention is understood as any kind of shoe, including (but not limited to) formal shoes, casual shoes, boots, sandals, etc. The invention is in particular suitable for sports shoes, such as (but not limited to) running shoes, tennis shoes, basketball shoes, soccer shoes, football shoes, rugby shoes, etc.

The at least one sensor may be a piezo element or a pressure sensor. Using sensor data from these kinds of sensors, it is possible to measure the weight of the person by measuring the force which is applied to the piezo element or the pressure sensor when the person stands, walks, or runs. Based on the weight it is possible to give the user health related messages (e.g. "train more", "your weight is higher than the last training", "train less as you are losing weight too fast"). Such messages could be based on a pre-entered body weight or based on a first measurement. The person could add weight ranges. Based on such ranges, messages (see above) could be send to the user. Based on the determined weight, a specific midsole and/or outsole with specific properties or materials could be amended or chosen. For example, the thickness of the midsole could be adapted to the weight of the user and the heavier the person is; the thicker the midsole could be to provide for sufficient cushioning. The outsole could be made more abrasion resistant if the person is rather heavy to counteract wear.

The digital model may be based at least in part on an analysis of the person's gait cycle by means of the received sensor data. The gait cycle contains important information like the amount of time the foot is in the air/on the ground, points in time of heel contact, pronation of the foot/feet, and push-off and the forces acting on the foot during the gait cycle. Based on this information, the customized sports shoe may be manufactured taking account the person's individual gait cycle.

The digital model may be based at least on one parameter of the group comprising the amount of time the person was running, the amount of time the person was walking, the amount of time the person was standing, the amount of time the person was sitting, the impact of forefoot strikes, the impact of midfoot strikes, the impact of heel strikes, pronation, stride distance, symmetry of the gait and weight of the person. These parameters provide for a good adaption to the person's individual characteristics.

The sports shoe may comprise a midsole and at least one parameter of the group comprising material, thickness, stiffness, insulation and/or cushioning properties of the midsole may be adapted based on the received sensor data. In this way, the midsole may be adapted to former sports activities in an optimal way. If, for example, the person mainly used streets with asphalt for running, the midsole could be provided with more cushioning.

The sports shoe may comprise an outsole and at least one parameter of the group comprising material, thickness, stiffness, cushioning properties, abrasion resistance and/or profile structure of the outsole may be adapted based on the received sensor data. In this way, the outsole may be adapted to particular sports activities in an optimal way. If, for example, the person mainly used forest tracks for running, an outsole with a deeper profile structure could be provided to improve traction.

The sports shoe may comprise an upper and at least one parameter of the group comprising material, thickness, stiffness, abrasion resistance and/or, water-proofness, air permeability, insulation and/or profile structure of the upper may be adapted based on the received sensor data. In this way, the upper may be adapted to former sports activities in an optimal way. If, for example, the person typically ran during rain, the upper may be provided with a water repellant textile, or in cold temperature the usage of a more insulating material.

The sensor data obtained by the at least one sensor may be stored on a server. The server may additionally store personal data. The server may be located in a cloud. Thus, the sensor data may be linked with personal data of the user, e.g. his gender and age. The digital model may then be based on such user data as well.

The sports apparel may further comprise at least one sensor which is capable to deliver sensor data for manufacturing a further sports apparel as described before. Thus, the sports apparel may be improved by each generation and may adapt to long-term variations of the person's characteristics in an iterative process.

A further aspect of the present invention relates to a method of manufacturing a first sports apparel customized for a person comprising the steps of: (a.) receiving sensor data obtained by at least one sensor integrated into a second sports apparel, wherein the sensor data is obtained while the second sports apparel is worn by the person during a sports activity; (b.) building a digital model of the first sports apparel based on the received sensor data; and (c.) manufacturing the first sports apparel based on the digital model.

The method of the present invention may be performed in a retail store. Thus, shipping and delivery of the apparel is omitted which may reduce the costs of the apparel. Furthermore, consumer experience is enhanced as the consumer may take his/her customized apparel immediately home.

In the context of the method of the present invention, the sensor data may include at least one parameter of the group comprising distance, speed, pace, heart rate, body temperature, temperature within the shoe, blood flow, energy expenditure and geographic position.

In the context of the method of the present invention, the at least one sensor may be at least one of a gyroscope, accelerometer, magnetometer, temperature sensor, pressure sensor, bending sensor, step counter, moisture sensor and positioning system (e.g. GPS, GLONASS, Galileo).

In the context of the method of the present invention, the sensor data may comprise sensor data from an accelerometer and a gyroscope.

In the context of the method of the present invention, the first sports apparel and the second sports apparel may be a sports shoe.

In the context of the method of the present invention, the digital model may be based at least in part on an analysis of the person's gait cycle by means of the received sensor data.

In the context of the method of the present invention, the digital model may be based at least on one parameter of the group comprising the amount of time the person was running, the amount of time the person was walking, the amount of time the person was standing, the amount of time the person was sitting, the impact of forefoot strikes, the impact of midfoot strikes, the impact of heel strikes, pronation, stride distance, symmetry of the gait and weight of the person.

In the context of the method of the present invention, the sports shoe may comprise a midsole and at least one parameter of the group comprising the material, thickness, stiffness, insulation and/or cushioning properties of the midsole may be adapted based on the received sensor data.

In the context of the method of the present invention, the sports shoe may comprise an outsole and at least one parameter of the group comprising material, thickness, stiffness, cushioning properties, abrasion resistance and/or profile structure of the outsole may be adapted based on the received sensor data.

In the context of the method of the present invention, the sports shoe may comprise an upper and at least one parameter of the group comprising material, thickness, stiffness, abrasion resistance and/or, waterproofness, air permeability, insulation and/or profile structure of the upper may be adapted based on the received sensor data.

In the context of the method of the present invention, the first sports apparel may comprise at least one sensor which is capable to deliver sensor data for manufacturing a third sports apparel according to a method as described before.

A further aspect of the present invention relates to a sports apparel manufactured according to a method as described before.

SHORT DESCRIPTION OF THE DRAWINGS

Figure 2:
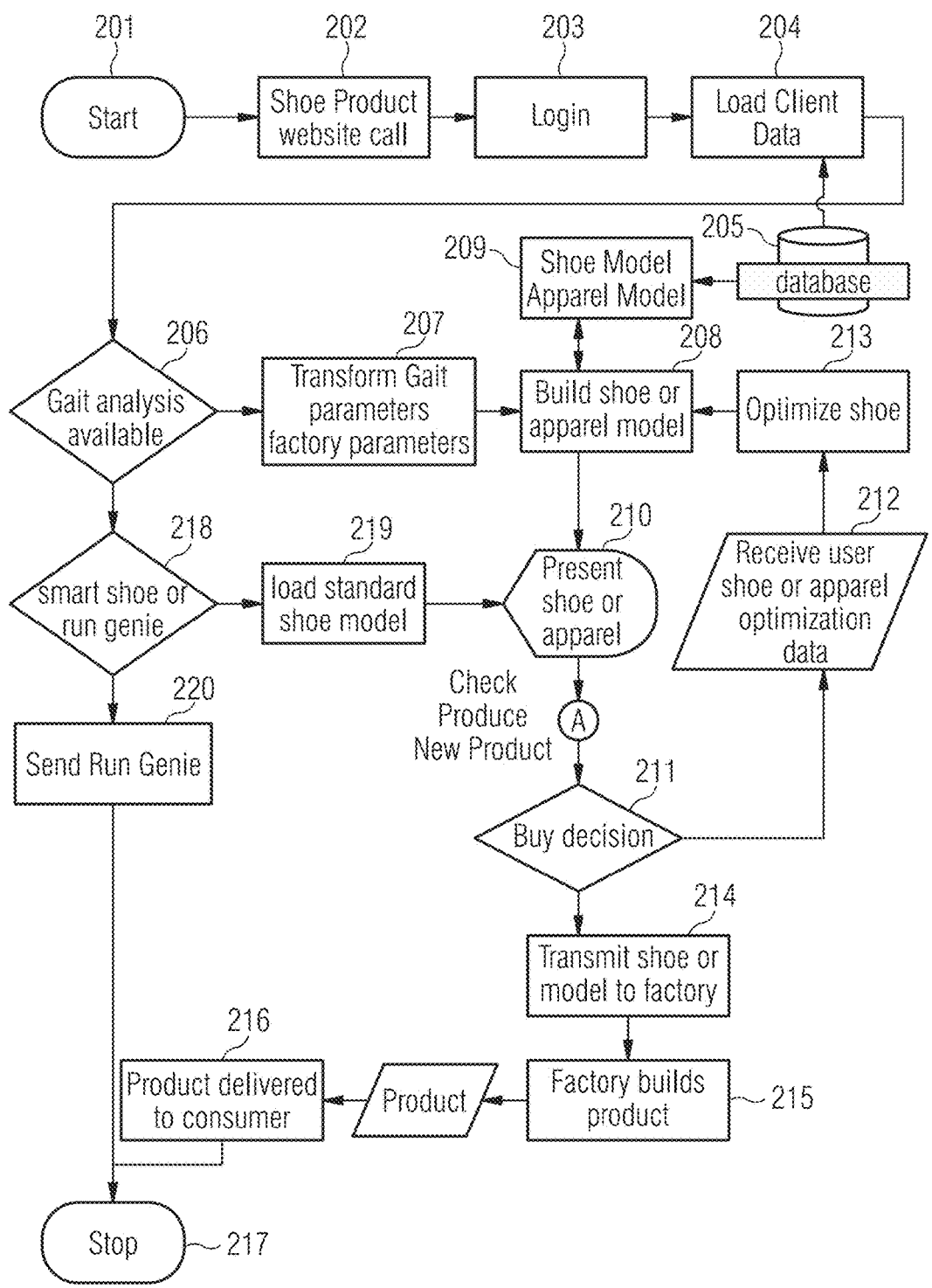
Figure 4:
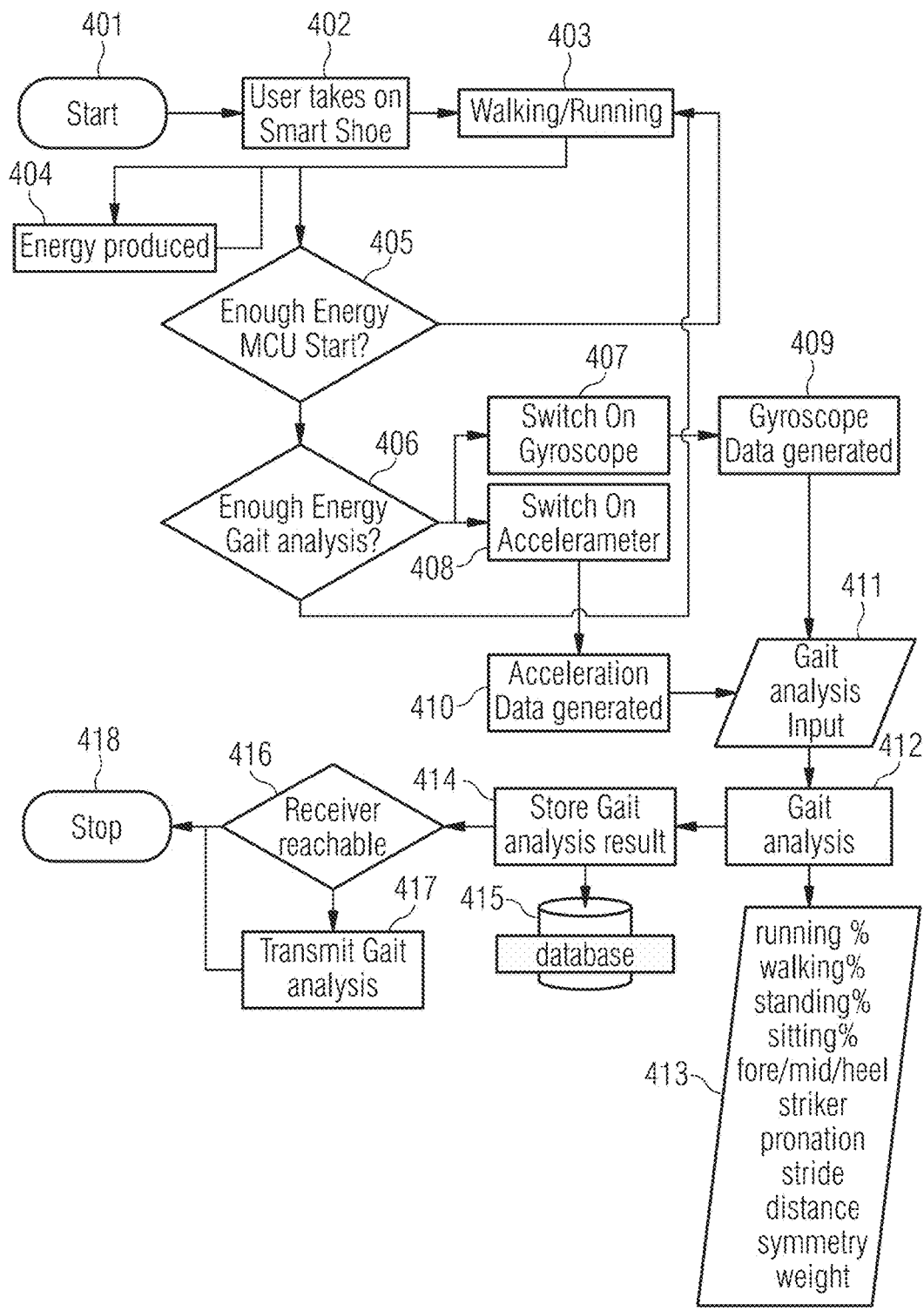
Figure 5:
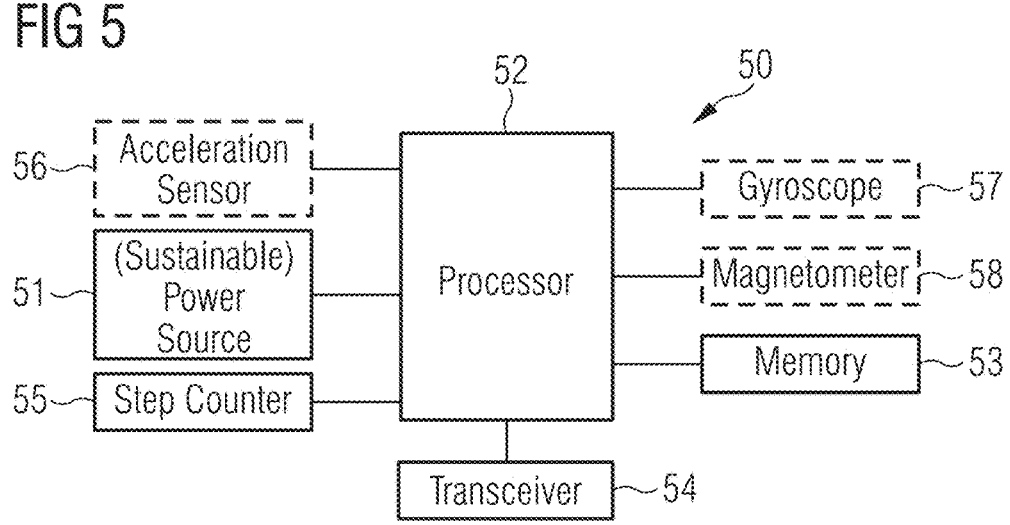
Figure 6:
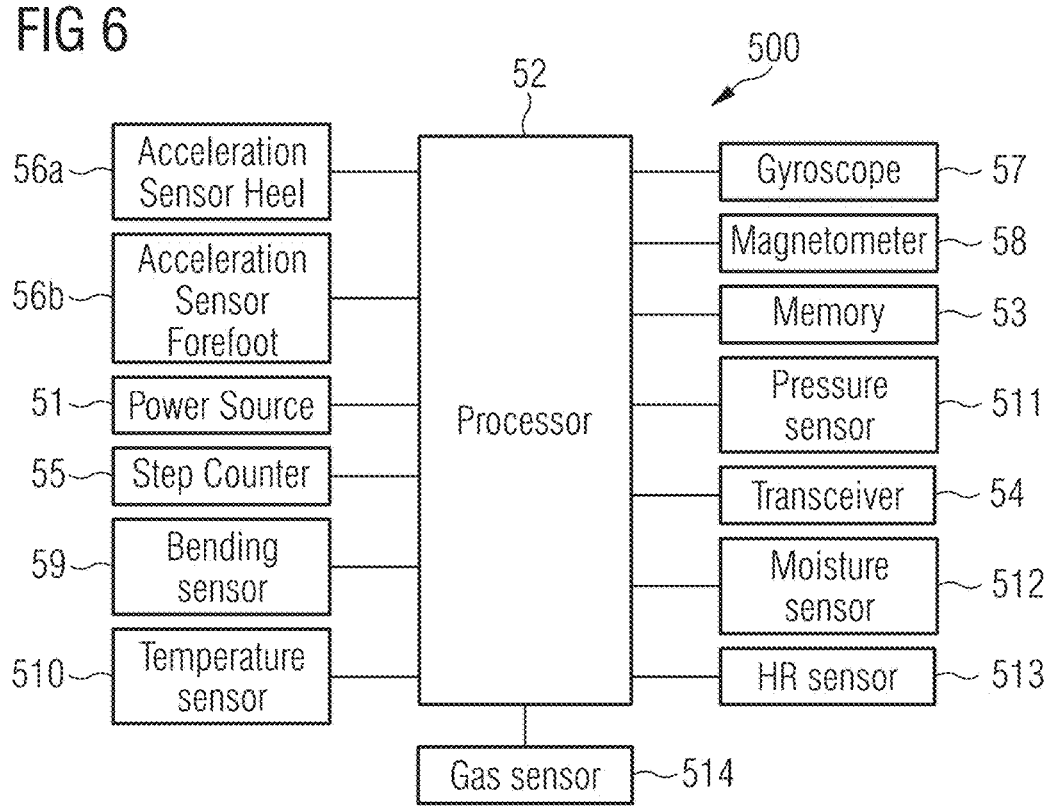
Figure 7:
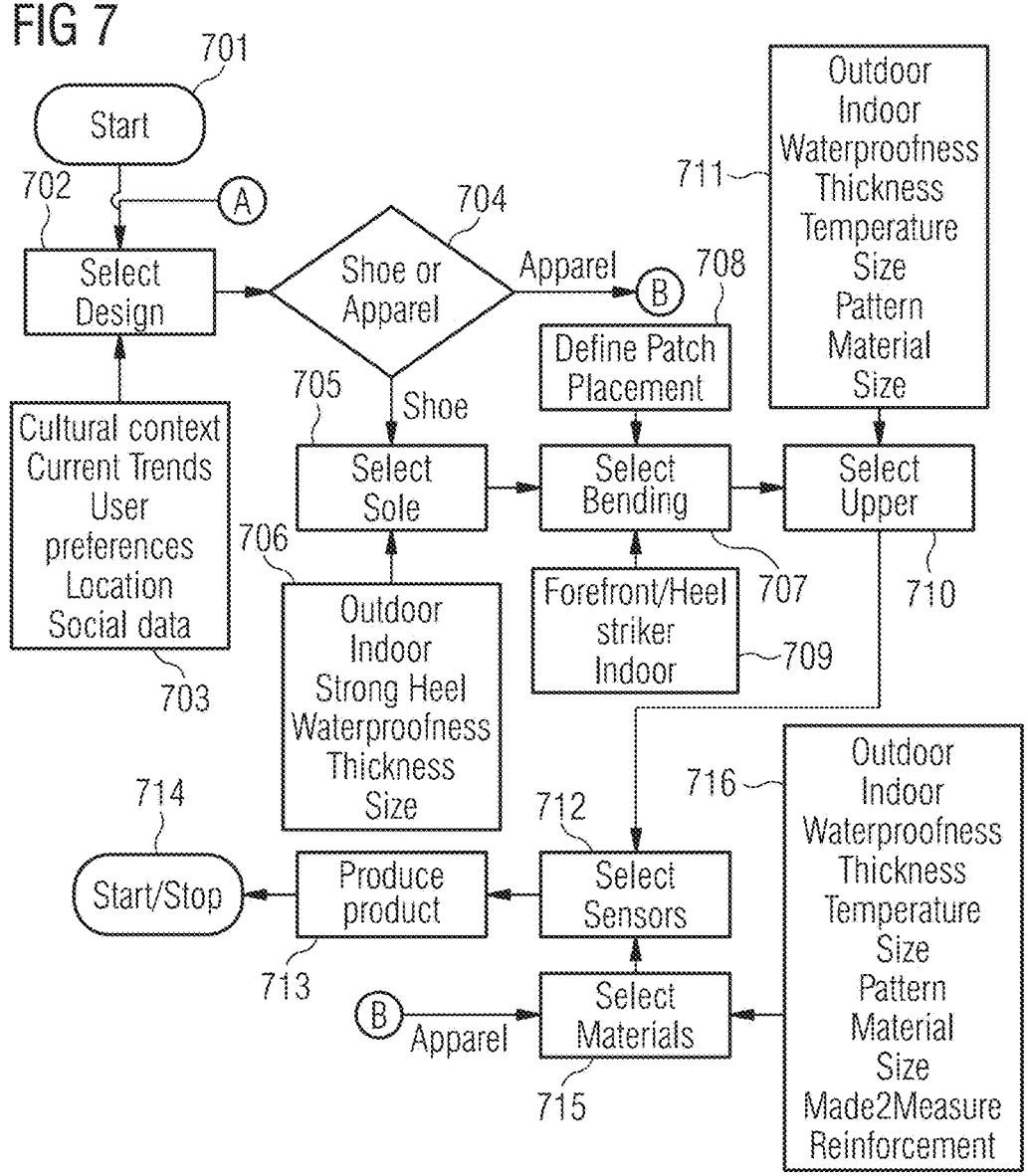
Figure 8A:
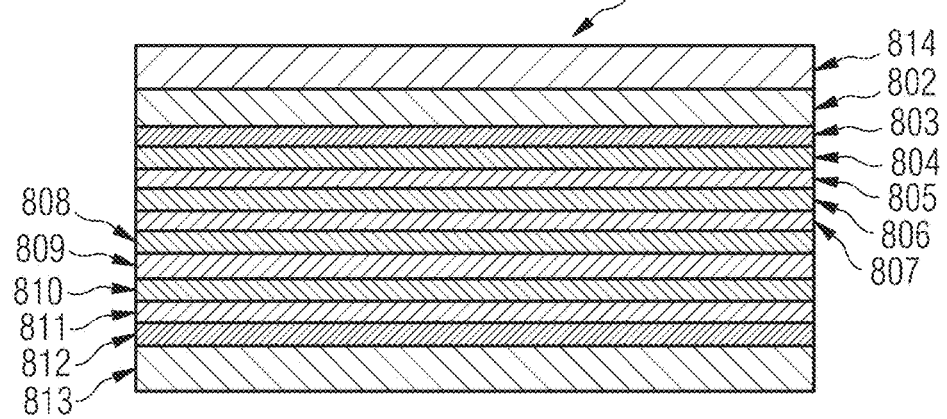
Figure 8B:
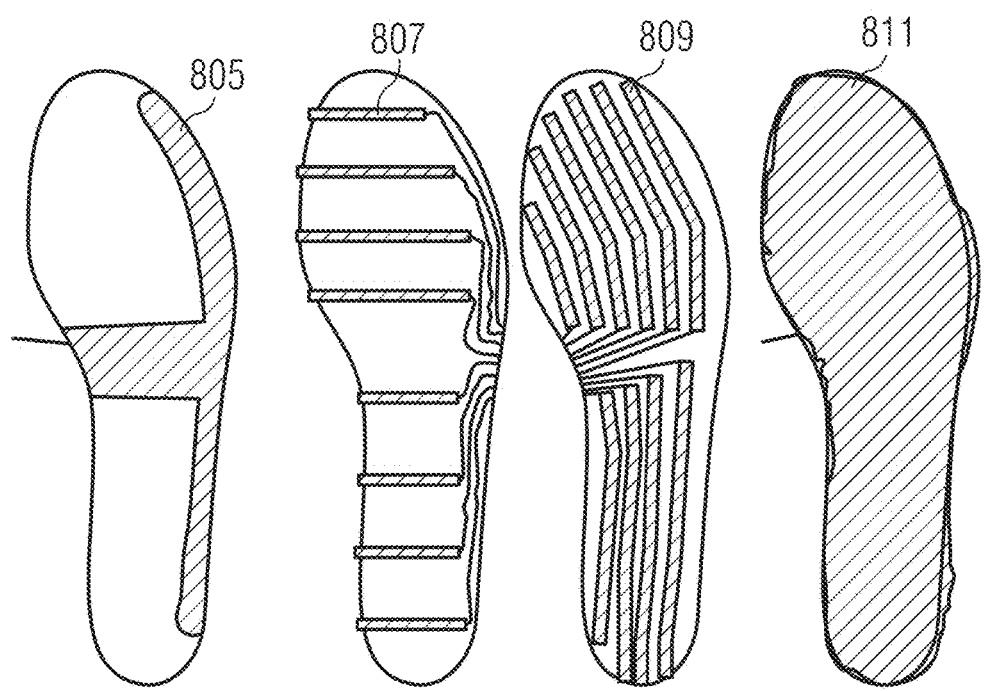
Figure 8C:
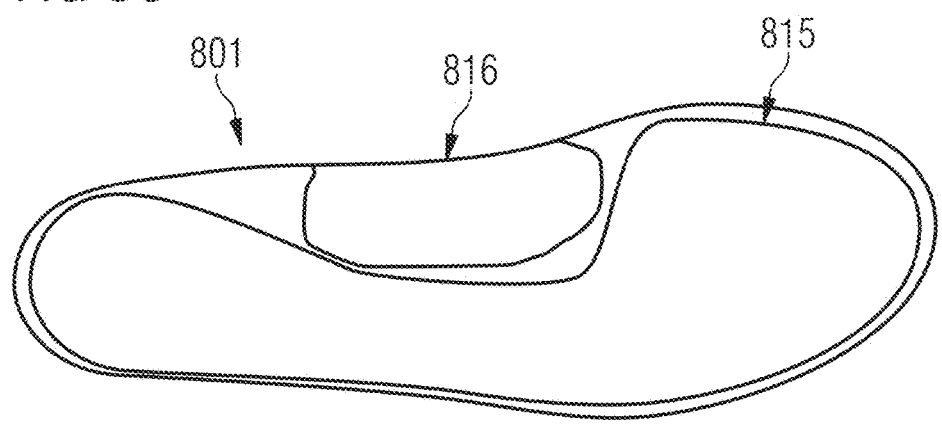
Figure 10A:
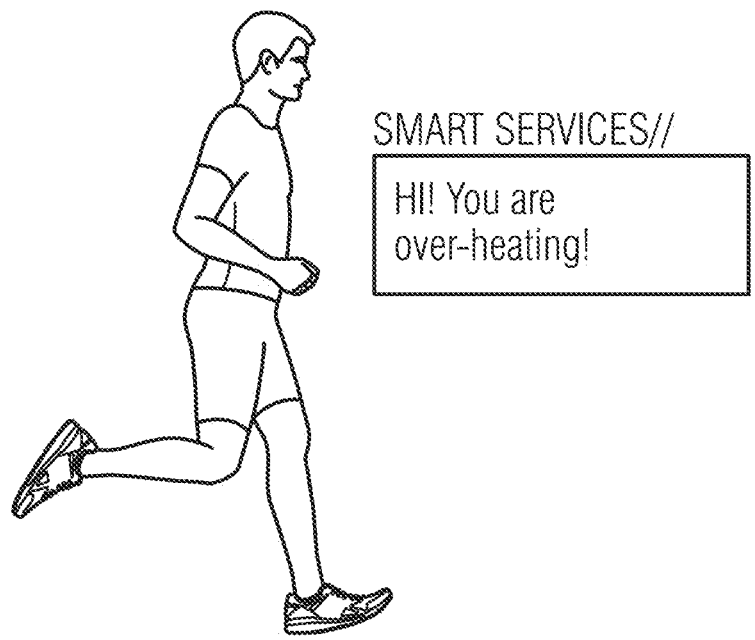
Figure 10B:
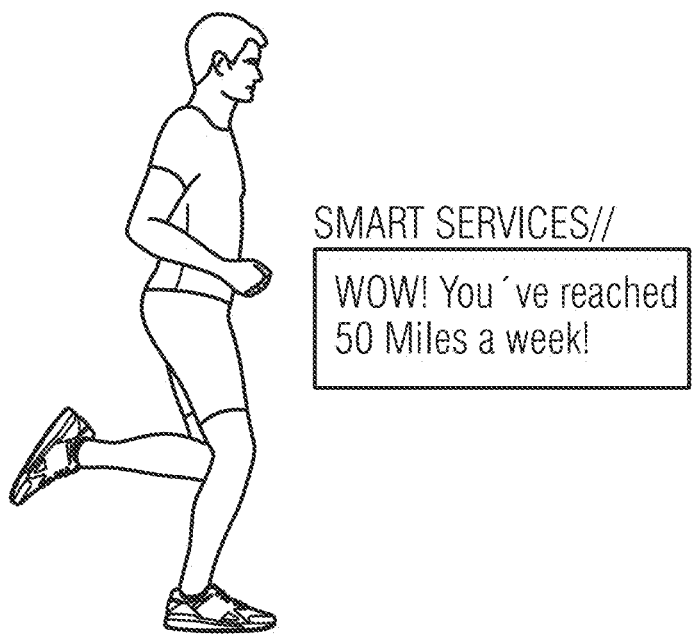
Figure 10C:
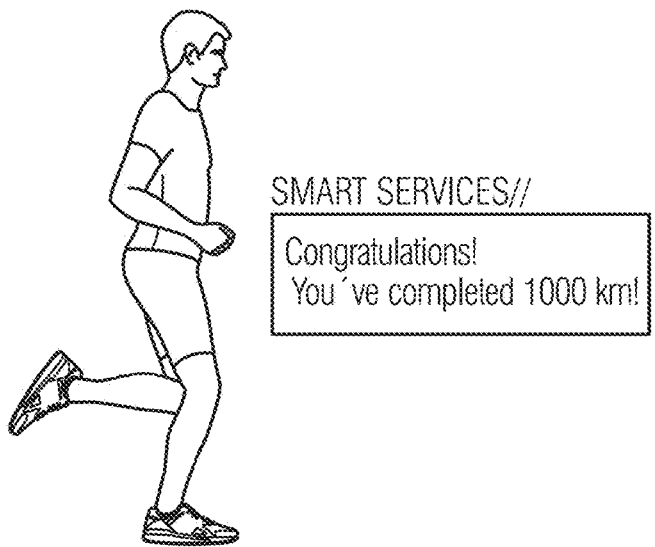
Figure 11:
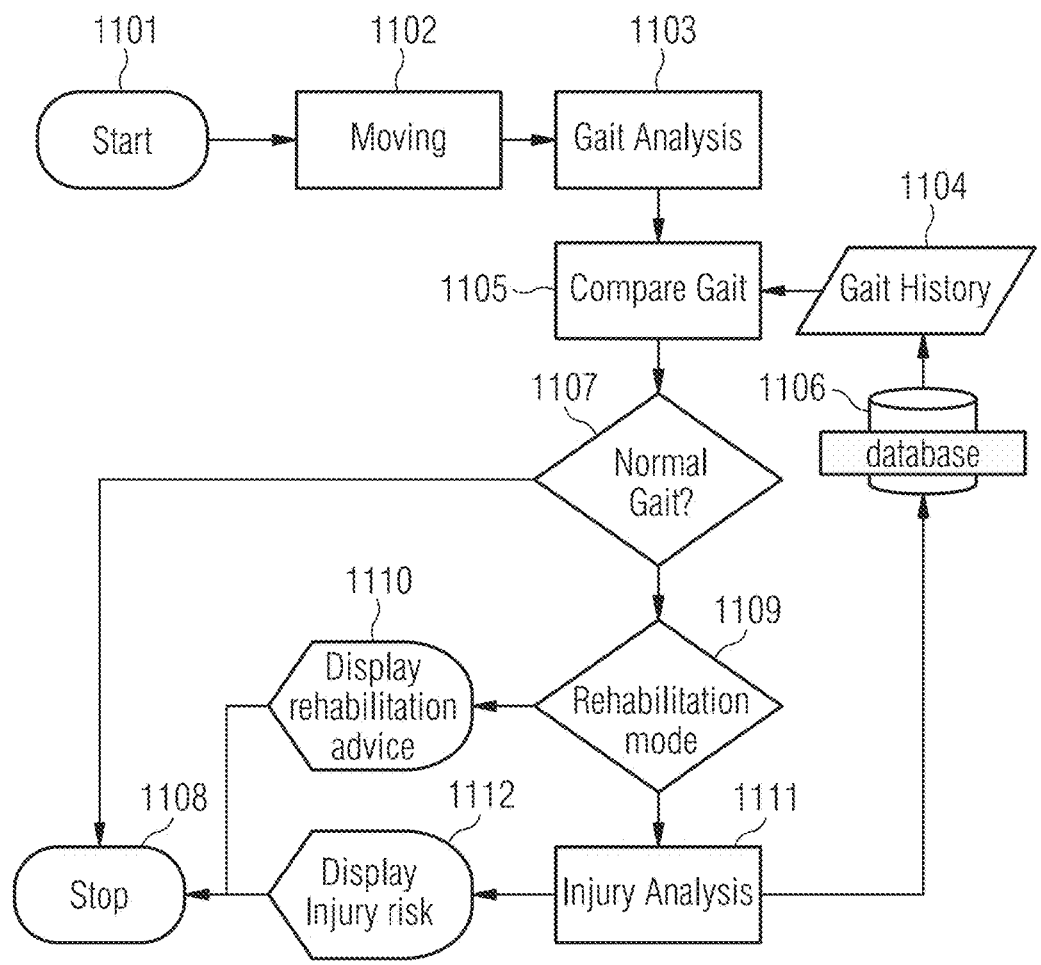

In the following, further aspects of the present invention are explained in detail referring to the figures. These figures show:

FIG. 1 exemplary schematic illustration of how a customized sports apparel according to the invention may be obtained;

FIG. 2 a more detailed schematic illustration of a process of how a customized sports apparel according to the invention may be obtained;

FIG. 3A to 3I examples of parameters which may be extracted from sensor data according to the invention;

FIG. 4 a schematic illustration of an exemplary process in the context of the present invention;

FIG. 5 a schematic illustration of electronic components integrated into a sports shoe for obtaining sensor data to be used in the context of the present invention;

FIG. 6 an example of a more complex sensor setup integrated into a sport shoe according to the present invention;

FIG. 7 a schematic illustration of an order process of a sports shoe customized for a person according to the present invention;

FIG. 8A to 8C schematic illustrations of an insole comprising a pressure sensor matrix which may be used as a sensor in the present invention;

FIG. 9 a use case scenario for the sports shoe and method ac-cording to the present invention;

FIG. 10A to 10C examples of messages presented to a user wearing a sensor based shoe; and FIG. 11 a schematic illustration of injury detection in the context of the present invention.

DETAILED DESCRIPTION OF THE FIGURES

FIG. 1 shows an exemplary schematic illustration of how a customized sports product (e.g. apparel) according to the invention may be obtained. The product in the example of FIG. 1 may be a customized sports shoe. However, the present invention is not limited to sports shoes. Rather, the invention may be practiced with any kind of sports apparel such as shirts, jerseys, sweaters, jackets, anoraks, pants, trousers, leggings, leotards, gloves, helmets, caps, belts, etc.

As shown in FIG. 1, a person buys a sensor based product (such as e.g. a running shoe), e.g., a product equipped with at least one sensor, in step 11. If the product is for example a shoe, the sensor(s) may for example be integrated into a midsole, outsole, insole or shoe upper of the shoe. For example, the sensor(s) may be removable placed, glued, sewn, welded, injection molded or otherwise integrated into the shoe. Examples of sensors will be given below. In some embodiments, the sensor based product may include only the sensor or sensor system.

In step 12 the sensor based product is used by the person. In this step, sensor data is obtained while the sensor based product is worn by the person during a sports activity. For example, a runner would use a sensor based shoe during running and the sensor integrated into the shoe would record sensor data, e.g., acceleration and pressure. The sensor data are not only specific for the person, but also for how he/she performs in his/her natural environment. Thus, the digital model of a new customized product (shoe) to be obtained and the customized product (shoe) itself may reflect the conditions under which the person typically performs a sports activity. For example the sensor data of an accelerometer and a pressure sensor may reflect that the person runs on hard asphalt tracks most of the time. Further examples of sensor data will be given below.

The obtained sensor data may be saved in a memory (which may also be located within the product/apparel/shoe, etc.) and/or may be directly transmitted to a device (e.g. a mobile device, computer, server, cloud memory, etc.) outside the apparel. Transmitting could be done via Bluetooth, BTLE, Wifi, NFC, cellular network transceiver or other transmission protocols.

In step 13 the information, e.g., the sensor data, is evaluated. For example, the sensor data may be preprocessed to remove noise, relevant sections of the sensor data corresponding to sports activities may be identified and relevant information to be used in later steps may be extracted. To this end, known techniques of preprocessing, digital filtering, feature extraction, statistical processing, machine learning, etc. may be used. Step 13 may also comprise deriving important information from the sensor date like for example usage (e.g. lifetime distance) of the product (e.g. shoe), average speed of the shoe, difference in altitude, maxi-mum speed, average pace of the shoe, maximum speed, temperature in the product (e.g. shoe) or at the skin of the person, pressure points within the product (e.g. shoe), a "heat map" (i.e. distribution) of pressure on the sole, etc. The pressure distribution can for example be used to understand the fitting of the product. In case of a shoe, if may be determined whether the shoe is too big or too small. High pressure on a lateral and/or a medial side of the sole can be an indication that the shoe does not have the proper size and/or should be customized such that it is a broader on the lateral and/or medial side.

Step 13 may be performed in the product/apparel/shoe, e.g. with a processor, microcontroller, ASIC, DSP, etc., or may be performed on a different device, e.g. a server, desktop computer, cloud server, etc. In the latter case, the sensor data may have been transmitted to the different device as described above.

In step 14 a new product model (e.g. a model of a shoe), e.g., a digital model of the customized product to be manufactured is build based on the received sensor data. As the digital model is build based on the received sensor data, it is possible to consider the individual anatomy and/or biodynamical properties of the person, in particular of his/her feet in case of a shoe. Examples of such properties and how they affect the customized product to be manufactured will be given below.

Step 14 may be performed on a mobile device (e.g. a mobile phone, smartwatch, tablet computer, etc. of the person), a computer of the person (such as a desktop computer or laptop), a computer in a shop/retail store. Step 14 may also be performed in the product (e.g. shoe) itself if it is equipped with proper computing capabilities. The digital model could be saved locally on the particular device and/or on a server and/or in a cloud. "Cloud" in the context of the present invention is understood as the storing of data in a remote computing center, but also the execution of programs which are not installed on a local device (e.g. smartphone, smartwatch, tablet computer, notebook, desktop computer, etc.) or server, but in the cloud.

The digital model may be a three-dimensional model of a shoe (or other sports apparel), like for example a model in a CAD system. The model may comprise information about which materials are used, their shape and dimensions, the kind and number of sensors, and their placement on the shoe. Step 14 also includes updating an existing digital model according to the obtained sensor data.

For example, the user may search in a database for existing shoe models or the user may get recommendations of existing shoe models from the computer system. The parameters of this model (e.g. shape of the shoe, materials used, patch placement, etc.) may then be updated based on the sensor data obtained with the already existing shoe in order to obtain a digital model for a new (improved) shoe.

Another example would be that the user may already have a sports shoe which was manufactured according to the invention. In this case, there exists already a digital model of this particular shoe. The parameters of this model (e.g. shape of the shoe, materials used, patch placement, etc.) may then be updated based on the sensor data obtained with the already existing shoe in order to obtain a digital model for a new (improved) shoe.

The digital model for the new shoe may also be customized according to the user's input. For example, the person may be asked which sensor(s) the new customized shoe shall have. The person may also be asked about the design of the shoe (e.g. colors, logos, applications, etc.) or its functional properties (e.g. waterproofness, cushioning, etc.). Or maybe the computer system makes a pre-selection or recommendation for the user which sensor(s) the new customized shoe shall have or the design of the shoe (e.g. colors, logos, applications, etc.) or its functional properties (e.g. waterproofness, cushioning, etc.).

In step 15 a customized product (e.g. a shoe) is produced based on the digital model. This allows the sports shoe to be manufactured by fully automated production techniques including 3D printing, placement of components by robots, knitting machines, etc. Such techniques are able to produce customized sports shoes at moderate costs and high throughput. Furthermore, it is possible to manufacture such customized sports shoes based on digital models not only in a factory, but also e.g. in a store.

The customized sports product (e.g. shoe) obtained in step 15 may be equipped with at least one sensor as well. Thus, this product (e.g. shoe) may be then used in step 12 during sports activities, e.g. during running, to obtain sensor data for a next generation of the product (e.g. a sports shoe) with further improved and customized characteristics. By this iterative process, the person may obtain a better product (e.g. sports shoe) in each generation of products (e.g. shoes). Furthermore, the products (e.g. sports shoes) may adapt to variations of the person's characteristic over time.

FIG. 2 shows a more detailed schematic illustration of a process of how a customized sports apparel according to the invention may be obtained. Also in this example, the sports apparel is a sports shoe. The process starts at step 201. In step 202 a person orders a sports shoe on a website of a sports equipment distributor. The person may already have login data from a previous purchase and enters this login data, e.g. user name and password, in step 203. The person may be identified by his/her username or other appropriate identification information, such that client data may be loaded in step 204. The client data may be loaded from a database 205 maintained by the sports equipment distributor or from server which may be located in a cloud. This database 205 may store all of the user data as described with respect to FIG. 1. This user data may form the basis for building the new shoe model.

At step 206 a determination is made whether a gait cycle analysis is available in the client data. The gait cycle analysis may be based on sensor data obtained from a sensor based shoe which the person already owns. For example, such a shoe may have been purchased by the person previously via the sports equipment distributor's website as mentioned before. The person may have used this sensor based shoe previously during running activities and at least one sensor in the shoe may have recorded sensor data. The sensor data may have been uploaded to the sports equipment distributor's database 205 as will be described in more detail below. Based on the uploaded sensor data a gait cycle analysis is performed.

The gait cycle analysis may also come from a manual entry by a shop assistant, e.g. based on a video analysis of the user. Furthermore, the gait cycle analysis may be based on sensor data obtained by a sensor which is clipped on a shoe as described in present applicant's patent applications with the application numbers U.S. application Ser. No. 14/579,226 and DE 15199781.4. These applications are hereby incorporated by reference in their entirety, for all purposes.

The general availability of such an analysis is checked in step 206.

The gait cycle analysis may be performed in the shoe itself. In this case, a powerful CPU may be integrated into the shoe which is capable of performing more advanced calculations as need by a gait cycle analysis. It is alternatively possible to store the sensor data in a memory in the shoe, transmit (e.g. via Bluetooth, BTLE, Wifi, NFC, a cellular network transceiver or other transmission protocols) the sensor data to a different device (like a smartphone, table computer, desktop computer, server computer, cloud computer, etc.) and have the gait cycle analysis done there. However, it should be considered that the sensor data can be rather big. For example, a single accelerometer may measure at 200 Hz, thus producing 200 data points per second. Thus, it is advantageous to do the calculations in the shoe.

If a gait cycle analysis is available in step 206, the process proceeds to step 207 in which parameters of the gait cycle analysis are transformed into factory parameters. For example the gait cycle analysis may reflect that the person runs on hard asphalt tracks most of the time. Accordingly, the factory parameters for a new customized running shoe would consider that a midsole with good cushioning characteristics would be needed. Further examples of how the parameters of a gait cycle analysis may affect the factory parameters for the new customized shoe will be given below.

At step 208 a digital shoe model of the new customized sports shoe is built based on the factory parameters obtained in step 207. As this step is similar to step 14 in FIG. 1, everything what has been described with respect to step 14 in FIG. 1 is applicable to step 208 of FIG. 2 as well. In this step it may be considered whether a shoe model 209 for a previous shoe ordered by the person is available in the database 205. The shoe model 209 may also be based on a digital model of a similar shoe. For example, if the user wants to buy a running shoe, an existing model of a running shoe may be used as shoe model 209. If a shoe model 209 is available, the previous digital shoe model may be considered when building the new digital model for the new customized shoe.

At step 210 the shoe model built in step 208 is presented to the person. For example, a 3D view of the shoe model may be presented to the person on a display screen, maybe in a window of a web browser or another suitable program. Another example is to present such a digital shoe model in an app running on a smartphone, smartwatch, tablet computer, digital media player, laptop computer, desktop computer or the like.

At step 211 the person may decide whether to buy a new customized shoe based on the digital shoe model presented in step 210. If the user is not yet satisfied with the present shoe, he may optimize the shoe, for example regarding the design, colors and materials used. It is also possible that the user adapts for example the cushioning properties, stiffness of the sole, waterproofness of the upper and the like. Consequently, at step 212 such shoe optimization data is received, for example via a web interface in a browser, suitable program or an app. In response to receiving the shoe optimization data the shoe is optimized at step 213 and an updated shoe model is built in step 208.

The person is given the opportunity to modify the shoe presented in step 210 before he/she decides to buy the shoe in step 211. This is indicated by the reference numeral "A" between step 210 and step 211 which refers to the corresponding reference numeral in the flow diagram of FIG. 7. The flow diagram of FIG. 7 illustrates how the shoe may be modified and customized. A detailed description of FIG. 7 will be given below.

If at step 211 the person decides to buy the shoe based on the shoe model presented in step 210, the digital shoe model created in step 208 is transmitted to a factory, shop or retail store in step 214.

In step 215 the new customized shoe for the person is built in the factory. The new customized shoe could also be built in a shop or retail store by corresponding production techniques. Fully automated production techniques including 3D printing, placement of components by robots, knitting machines, etc. may be used to build the shoe (especially in a shop or retail store), but it also possible that all or part of the manufacturing is performed manually.

The shoe built in step 215 is then delivered to the person at step 216 for example by a parcel service at which point the process depicted in FIG. 2 terminates at step 217. If the shoe is built in a shop or retail store, the finished shoe is passed to the customer.

Coming back to step 206, if no gait cycle analysis is available for the person, a decision about alternative ways to obtain a gait cycle analysis is made in step 218.

If in step 218 a decision is made in favor of a customized shoe according to the invention (a "smart shoe") then a standard shoe model is loaded in step 219 which is presented to the user in step 210 described before. If in step 218 a decision is made in favor of different way to produce a sports shoe then the procedure proceeds to step 220.

In step 220 a sensor is provided to the user which may be clipped on a shoe. The gait cycle analysis may then be based on sensor data obtained by the sensor which is clipped on a shoe during running as described in present applicant's patent applications with the application numbers U.S. application Ser. No. 14/579,226 and DE 15199781.4, as above. Such a sensor may be given to the person in a shop or retail store.

An alternative way of obtaining a gait cycle analysis is a video analysis of the person running on a treadmill which could be done in a shop or retail store.

FIGS. 3A to 3I illustrate parameters which may be extracted from sensor data to manufacture a first customized sports apparel according to the invention. The sensor data may be obtained by at least one sensor integrated into a second sports apparel while the second apparel is worn during a sports activity by the person for which the first customized sports apparel is to be manufactured. In the example of FIGS. 3A to 3I the sports apparel is a running shoe and the sports activity is running. However, as already mentioned, the present invention may be practiced with any kind of sports apparel such as shirts, jerseys, sweaters, jackets, anoraks, pants, trousers, leggings, leotards, gloves, helmets, caps, belts, etc. Also, the sports activity may be different and may for example be hiking, soccer, rugby, football, basketball, volleyball, cycling, swimming and the like.

Figure 3A:
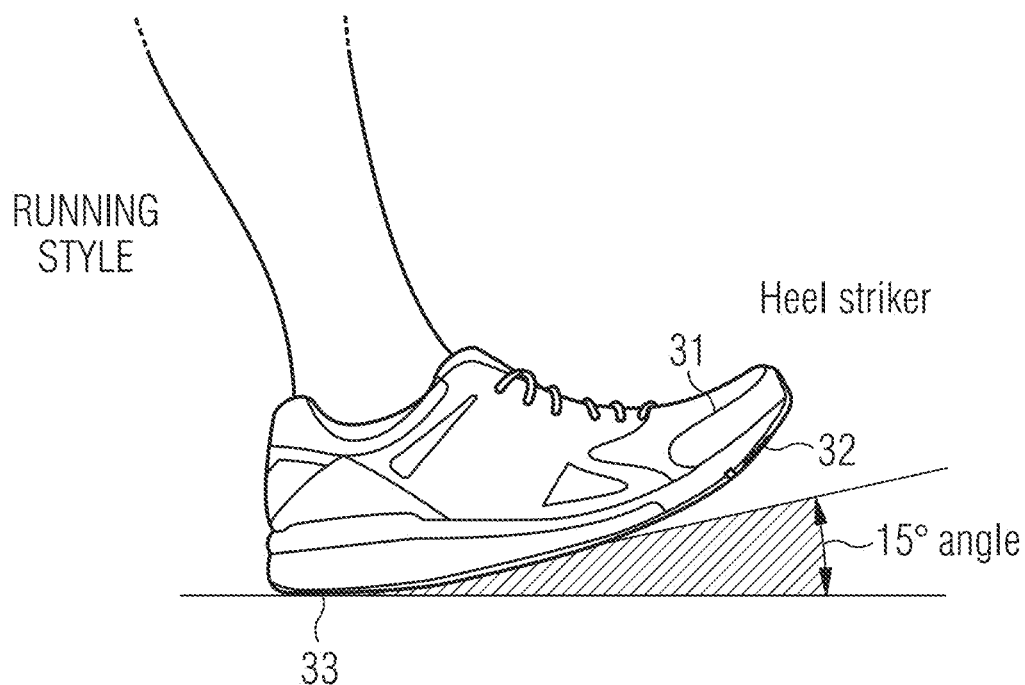

As illustrated in FIG. 3A, one parameter which may be extracted from sensor data is the running style of the person. In this example "running style" refers to the angle of the bottom side of the outsole 32 of the shoe 31 relative to the ground 33 when the foot touches the ground. In the example of FIG. 3A the angle is 15°. Therefore, the person is considered to be a "heel striker". In this case, the customized sports shoe manufactured according to a digital model based on the sensor data may comprise more cushioning in the area of the heel and/or the profile or shape of the outsole, maybe especially in the area of the heel. "Running style" may also refer to whether the person overpronates, supinates, or is a neutral runner. In general, the running style may be detected by a combination of an accelerometer and a gyroscope (plus magnetometer in certain applications) or by a combination of accelerometer and magnetometer or by an accelerometer alone.

In order to be able to measure the angle of the outsole at the point of time when the heel hits the ground 33, the running shoe 31 may be equipped with an accelerometer and a gyroscope. Data from the accelerometer allows to determine the impact of the heel on the ground, whereas data from the gyroscope allows to determine the orientation of the shoe during such impact.

Figure 3B:
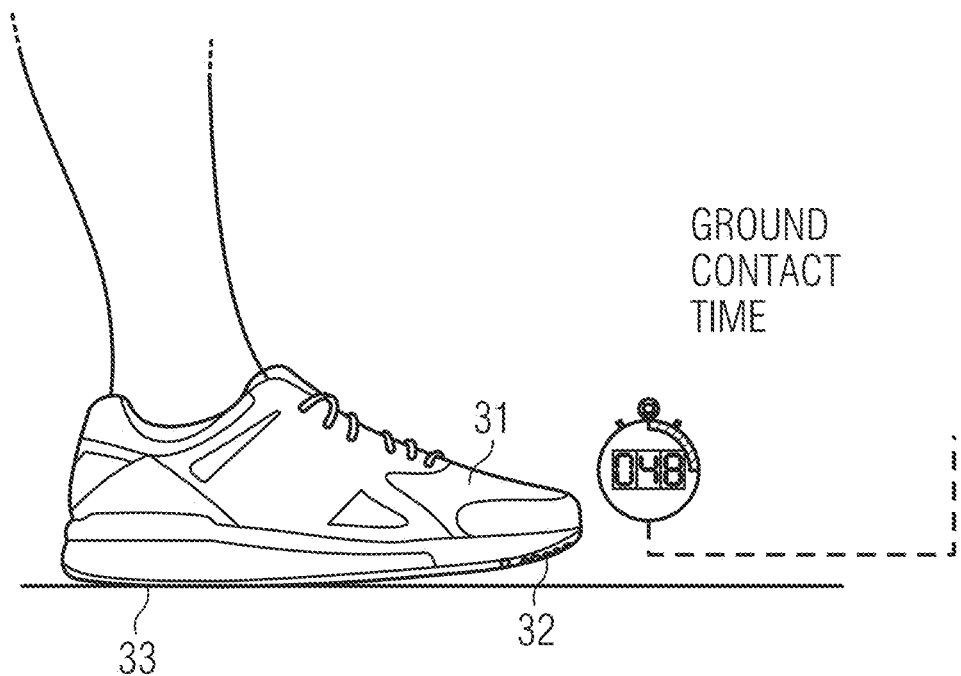

FIG. 3B illustrates a further parameter which may be extracted from sensor data, namely the ground contact time which corresponds to the duration of time the outsole 32 of the shoe 31 contacts the ground 33 during a gait cycle. To measure ground contact time, an accelerometer may be used to detect time periods in which the shoe 31 is at rest, such as during ground contact. Alternatively, or -additionally, data from a pressure sensor in the outsole, midsole or insole may indicate when the foot is resting on the ground.

Typically, ground contact time can give the runner a feedback about his running style. Based on the ground contact time it also possible to derive, possibly based on a calibration, the speed, distance, and/or pace of the person. These parameters can be used to let the person know when the shoe is worn out or to provide the person with performance data, like speed, distance, pace, etc. Furthermore, during times of no contact with the ground, a processor in the shoe may be put into sleep mode as mostly the ground contact time is important to measure with all the sensors. Hence battery power can be saved based on this information.

Figure 3C:
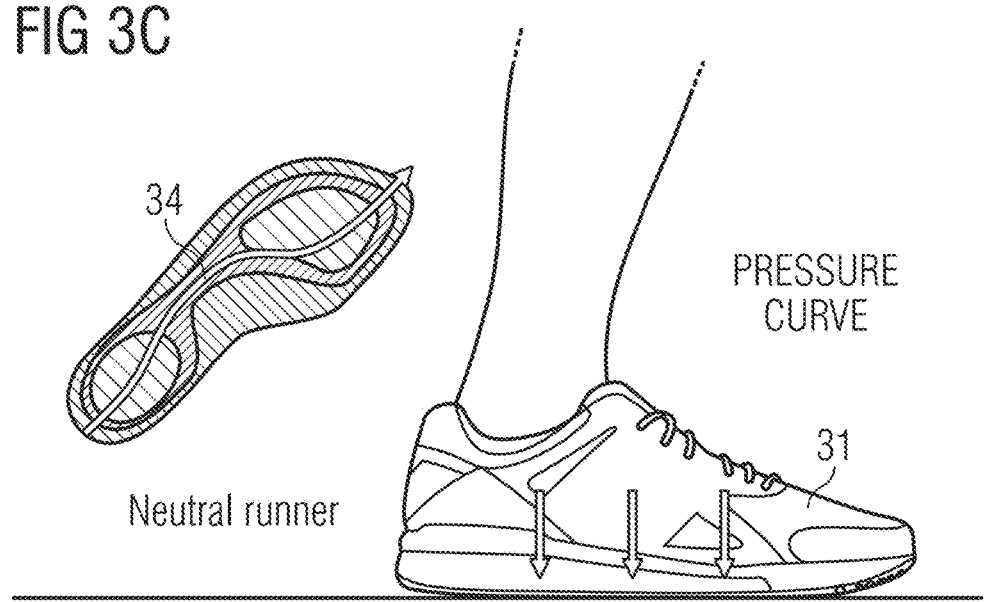

A further parameter which may be extracted from sensor data is the pressure curve as illustrated in FIG. 3C. The pressure curve is based on the distribution of pressure 34 along the sole of the shoe 31 during ground contact as illustrated on the left side of FIG. 3C. Based on the pressure curve a determination may be made of whether the person wearing the shoe 31 overpronates, supinates or is a neutral runner as in the example of FIG. 3C. The customized sports shoe manufactured according to a digital model based on the sensor data may then be equipped with a pronation support, supination support or may be a neutral running shoe. Furthermore, the customized shoe can also be built with specific insole, midsole and/or outsole material, specific cushioning material in specific areas or a specific profile on the outsole, all based on the pressure curve. For example, the insole may be made from a soft foam material, a stiff foam material, or a combination of both, eTPU/ePEBA material, EVA material, or any combination of several materials. Likewise, the midsole may be made from a soft foam material, a stiff foam material, or a combination of both, eTPU/ePEBA material, EVA material, or any combination of several materials. The outsole may be made from rubber having certain properties, e.g. sticky, non-marking, non-sticky, etc.). Different combinations of material and/or material properties may be used for the outsole.

The pressure curve may be measured by means of a pressure sensor as for example described herein with respect FIGS. 9A, 9B and 9C. The pressure curve can for example be used to understand the fitting of the product. In case of a shoe, if may be determined whether the shoe is too big or too small. High pressure on a lateral and/or a medial side of the sole can be an indication that the shoe does not have the proper size and/or should be customized such that it is a broader on the lateral and/or medial side.

Figure 3D:
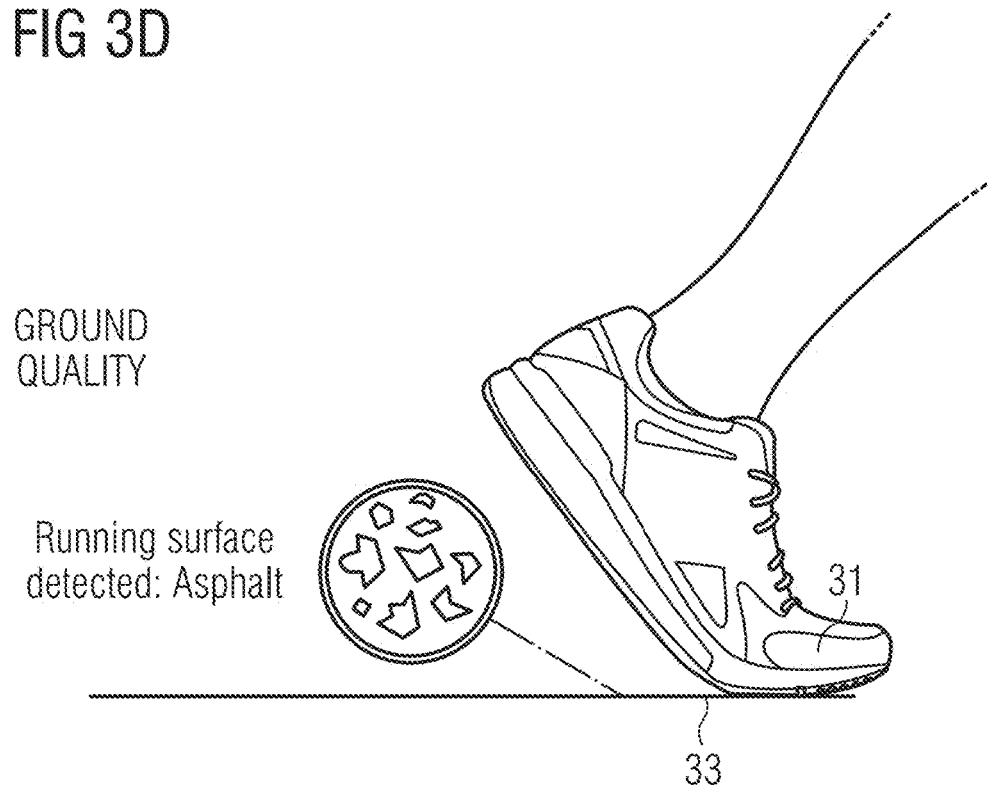

FIG. 3D illustrates a further parameter which may be extracted from sensor data, namely the ground quality, e.g. whether the person is or was running on soft ground like a forest track or hard ground like a street, paths, tracks with asphalt as in the example of FIG. 3D. The customized sports shoe manufactured according to a digital model based on the sensor data may then be adapted to the ground quality which the person usually faces. If for example he/she is running on asphalt most of the time, the midsole of the customized sports shoe may be provided with more cushioning. Data on the ground quality may be measured for example with an accelerometer or a pressure sensor, a combination of accelerometer and gyroscope or a combination of accelerometer and pressure sensor.

Figure 3E:
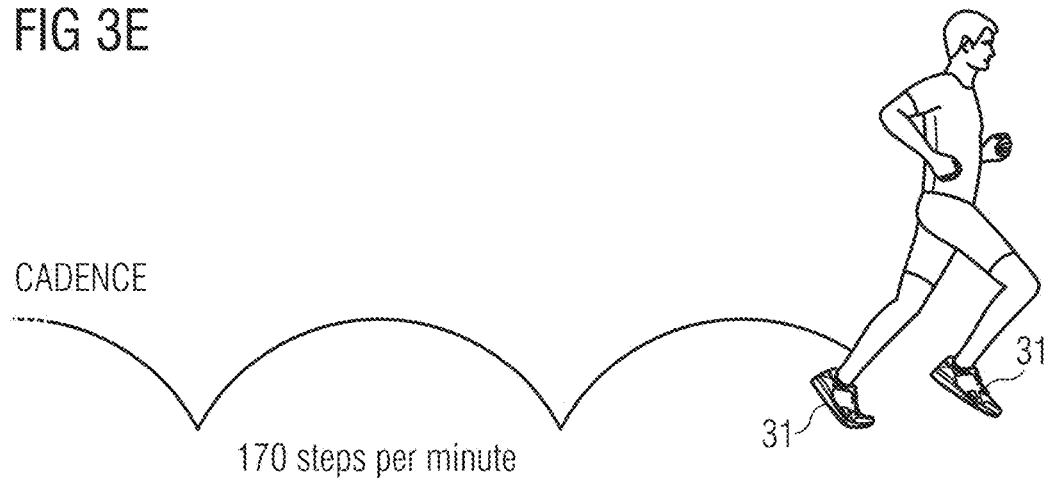

A further parameter which may be extracted from sensor data is cadence which is illustrated in FIG. 3E. Cadence refers to the number of steps per minute which in the example of FIG. 3E is 170 per minute. Cadence may reveal information about the person's running style. For example one person may vary cadence to increase speed, whereas another person may vary the stride length to increase speed. Cadence may be measured by means of an accelerometer or a pressure sensor to detect the ground contact during each gait cycle.

Figure 3F:
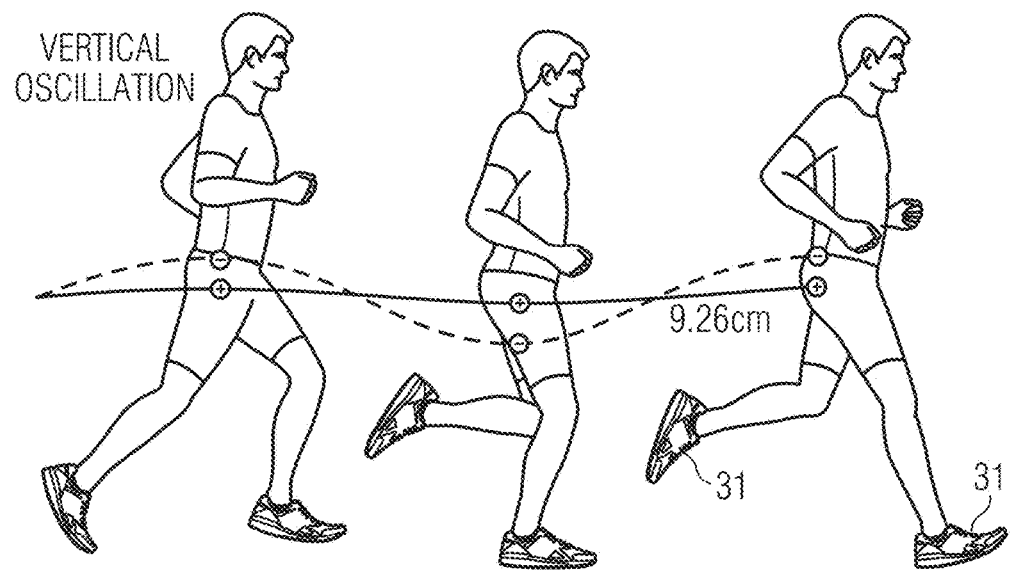

FIG. 3F illustrates a further parameter which may be extracted from sensor data, namely the vertical oscillation which is the distance between the lowest and highest position of a fixed-point on the body, for example the hip. Performance is a factor related to vertical oscillation. The higher the vertical oscillations, the more cushioning is needed in the shoe. Furthermore, predictive shoe maintenance in relation to body characteristics will become important capabilities from a consumer perspective. For example, the shoe may signal the mileage to the user, and prevent injuries. In one exemplary scenario if the user would run under the same conditions for further 2 km, his knee would start to suffer, so the shoe may recommend to go for a replacement or maintenance, e.g. to refurbish the outsole. Very high oscillation is creating more pressure on the shoe and is probably reducing the lifetime of the shoe. So this kind of information can be used to predict the wear of the shoe and advise the user on that.

If the at least one sensor is a temperature sensor, temperature information may be obtained as illustrated in FIGS.

Figure 3G:
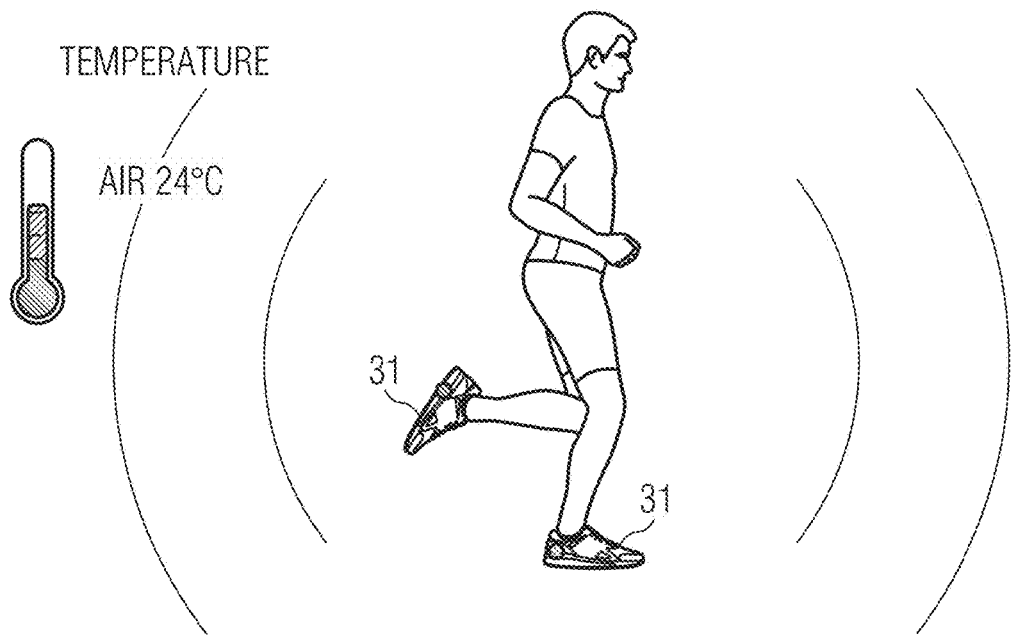
Figure 3H:
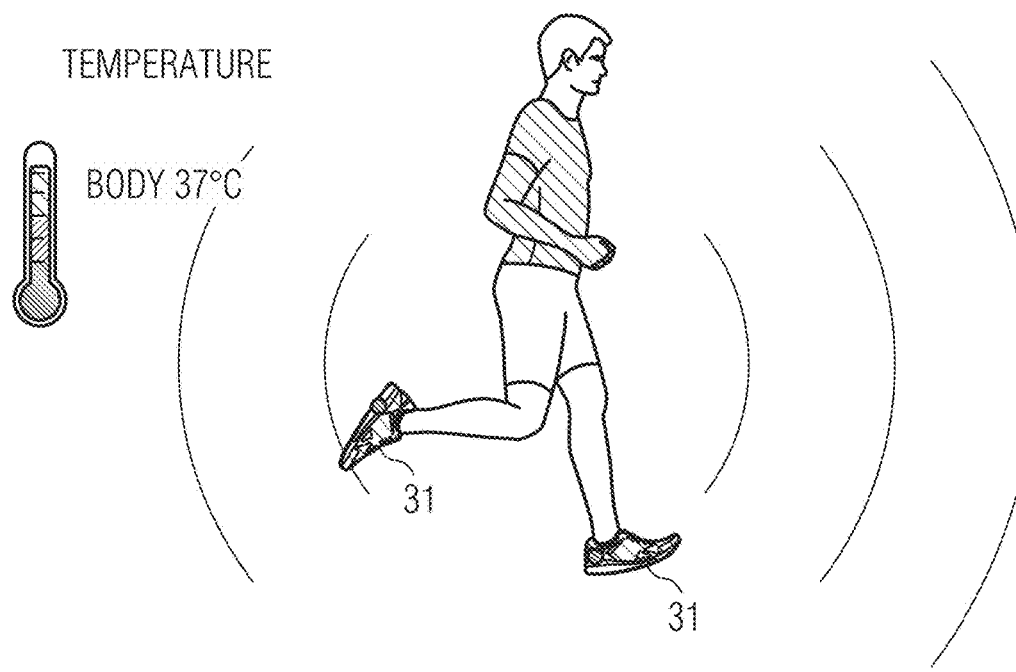

3G and 3H. In FIG. 3G the temperature is measured by means of at least one temperature sensor integrated into the running shoe 31 but facing the outside. In FIG. 3H the body temperature is measured by means of at least one temperature sensor integrated into the running shoe 31 close to the wearer's foot. The customized sports shoe manufactured according to a digital model based on the sensor data may be adapted to the average outside and body temperature conditions measured with the temperature sensors. If for example the person's temperature tends to be rather high during running, the upper of the sports shoe may be provided with lightweight and cooling materials and/or with ventilation openings.

FIG. 3I illustrates a temperature sensor integrated in a running shirt. The sensor measures the temperature of the upper body of the person which in the example is at 37° C. The data measured by the temperature sensor may be used together with sensor data gathered in a shoe as described previously with respect to FIGS. 3A to 3H. For example, if there is a discrepancy between (upper) body temperature and the temperature measured inside the shoe, the material of the customized shoe to be built may be adapted accordingly. If for example the temperature inside the shoe is always above the body temperature, the material for the shoe upper may be made more lightweight and air permeable to permit a good ventilation of the foot.

A temperature sensor in a sports apparel like a shirt may detect the body temperature to recommend the user after a sports activity (e.g. a run) and/or before a sports activity (e.g. a run) a new (different) shirt which may be made of a cooling material (to help to cool down the body) or a more insulating material (to help maintaining the body temperature). Additionally the air (ambient) temperature could also be measured by an external device of the person or could be gathered from a server via an internet connection. Based on the body temperature and the air temperature a recommendation for a perfect shirt can be given.

This is helpful for preventing overheating or cooling down too quickly.

FIG. 4 shows a schematic illustration of an exemplary process in the context of the present invention. The process starts at step 401. In step 402 a user takes on a "smart shoe", i.e. a shoe equipped with at least one sensor. In the example of FIG. 4 the shoe is equipped with a gyroscope and an accelerometer and an energy harvesting module.

In step 403 the user walks and/or runs with the shoe. While the user is walking and/or running, energy is produced by an energy harvesting device integrated into the shoe as illustrated at step 404. Such an energy harvesting device may for example be based on a piezo element which produces a current as pressure is applied thereon. The current may be used to charge an accumulator or capacitor. At step 405 a decision is made whether enough energy has been produced by energy harvesting to start a microcontroller (MCU). For example, if the charge stored in a capacitor crosses a certain level, the microcontroller may start up.

If the energy produced at step 405 is sufficient to start the microcontroller, the microcontroller is started. Then, a determination is made at step 406 of whether the energy is sufficient to perform a gait cycle analysis by the microcontroller. If the energy is sufficient, the gyroscope and the accelerometer are switched on at steps 407 and 408, respectively. While the user keeps on walking and/or running, the gyroscope generates gyroscope data as illustrated by step 409 and the accelerometer generates acceleration data as illustrated by step 410. Gyroscope data and accelerometer data are used as input for a gait cycle analysis as illustrated by step 411. A gait cycle analysis is then performed at step 412.

The gait cycle analysis may extract parameters like the amount of time the user is running (in percent of total time), the amount of time the user is walking (in percent of total time), the amount of time the user is standing (in percent of total time), the amount of time the user is sitting (in percent of total time), whether the user is a forefoot striker, a mid striker or a heel striker, pronation, stride distance, symmetry of the gait and the weight of the user. This is illustrated in step 413. At step 414 the results of the gait cycle analysis may be stored in a memory (maybe a temporally memory) which is connected with the sensors. The saved data may then be transmitted to a database 415, which could also be seen as a cloud where several other devices have access to. It would also be possible, if a receiver is reachable 416 to transmit 417 the gait analyses (412, 413) to a mobile device of the person to see the extracted parameters on the display (not shown in FIG. 4). The transmitting to the database 415 or to a receiver 417 can be done via BTLE, Bluetooth, Wifi, NFC, cellular network transceiver or any other wireless transmitting protocol. It may also be possible that the raw data or preprocessed data are saved/transmitted to the database or the receiver or the memory for a later processing.

At step 416 a determination is made of whether a receiver is reachable. If this is the case, the gait cycle analysis is transmitted in step 417 and the process terminates at step 418. The mentioned receiver could be the receiver or transceiver of a smartphone, tablet, computer, etc. The receiver could also be integrated in a router. With Bluetooth 4.2 enabled routers it is possible to transmit data directly to routers, so sensor data may be offloaded as soon as possible from the device as it has limited storage.

FIG. 5 is a schematic illustration of a sensor device 50 (removable or not removable) integrated or attached into a sports shoe for obtaining sensor data to be used in the context of the present invention. To supply electric power to the electronic components, a power source 51 is integrated into the shoe. This power source could be a battery or rechargeable battery which could be removable. An example of a sustainable power source is a piezo element which generates electric power from pressure variations during running or walking with the sports shoe, a technique which is denoted as energy harvesting.

The sensor device 50 in the example of FIG. 5 may comprise a processor 52 for preprocessing or processing sensor data received from one or more sensors, like described below. For example, the processor 52 could preprocess or evaluate the sensor data and/or perform a gait cycle analysis as described before. The processor 52 is connected to a memory 53 for storing computer instructions and/or data. For example, the received sensor data could be stored in the memory 53 either in raw format or after preprocessing by the processor. Also, results of the gait cycle analysis could be stored in the memory 53.

To transmit the sensor data, results of a gait cycle analysis, etc. from the shoe to another device for creating a digital model of a customized shoe or processing performance data out of the sensor data, the sensor device 50 comprises a transceiver 54. The transceiver 54 could be a Bluetooth, Bluetooth Low Energy (BTLE), Wifi, NFC, cellular network transceiver or the like. It would also be possible to exchange the transceiver with a transmitter to transmit the data like described above. Also, it is possible to transmit the data via a wired connection in which case the transceiver 54 would be a driver for a USB or serial connection for example.

In a minimal setup, the shoe comprises a step counter 55 which is able to count the steps taken by the user while he/she is running or walking. Using data from the step counter 55 it is at least possible to determine whether the user is an intensive runner, i.e. how often he/she runs and how long such a run lasts on average. Furthermore, it is possible to extract the pace, i.e. steps per minute. This information may be used in the context of the present invention to build a digital model of a customized sports shoe and to manufacture such a customized shoe based on the digital model. If, for example, the user turns out to be an intensive runner with a high pace, the customized shoe could be provided with more or less cushioning characteristics to avoid injuries. The step counter may be based on an accelerometer and/or at least one piezo element In a more advanced setup, the shoe is equipped with an acceleration sensor 56 and a gyroscope 57 as indicated by the dashed boxes in FIG. 5. Data from these sensors allow a more advanced analysis of the person's gait cycle. In fact, such a setup uses the lowest power for a gait cycle analysis. The power for such a setup could be provided by energy harvesting techniques as described above. In an alternative setup the shoe comprises an acceleration sensor 56 and a magnetometer 58 to allow for a gait cycle analysis. It is also possible to have all three sensors, i.e. acceleration sensor 56, gyroscope 57 and magnetometer 58 integrated into a shoe which would deliver best results for a gait cycle analysis. In general, it is possible to use only one of the sensors shown FIG. 5, two of those sensors or all three.

FIG. 6 shows an example of a more complex sensor device 500 removable or not removable integrated or attached to a sport shoe according to the present invention. This example includes a power source 51, processor 52, memory 53, transceiver 54 and step counter 55, gyroscope 57 and magnetometer 58 similar function as described to the setup shown FIG. 5. Additionally, the example of FIG. 6 comprises separate acceleration sensors for the heel of the foot and for the forefoot, 56a and 56b, respectively. Thus, acceleration may be measured more accurately and differences between forefoot and heel acceleration may deliver more detailed information for building a digital model of a customized shoe according to the invention. In general, according to the invention any number (including just one) and combination of the described sensors may be used. Thus, not all sensors shown in 6 may be present and/or used.

The exemplary sensor device 500 of FIG. 6 comprises a bending sensor 59. Such a sensor is able to measure the bending of the shoe, e.g. of its sole. A temperature sensor 510 may measure the outside air temperature and/or the temperature of the person's body or the temperature in the shoe when wearing the shoe.

Pressure sensor 511 is a pressure sensor matrix like the one which will be described in more detail in FIGS. 9A, 9B and 9C. Using such a pressure sensor matrix, it is possible to obtain a series of "pressure maps" (similar to so called "heat maps") that encode the dynamics of how the foot behaves while moving, i.e. the distribution of pressure over time. This information may enable real-time interactions with the user like for example advises to correct movement while running to prevent injuries.

Moisture sensor 512 is able to measure the moisture inside the shoe and/or outside. Moisture data from inside the shoe may provide information about the person's perspiration. If perspiration is high, the customized shoe may be provided with moisture wicking materials and/or good air ventilation. Moisture data from outside the shoe may indicate whether the person typically runs in bad weather conditions such as rain. If this is the case, the customized shoe may be provided with water repellent coatings.

Heart rate (HR) sensor 513 is able to measure the person's heart rate which may allow to infer the person's fitness level.

Gas sensor 514 may give an indication about the sweat consistence. This may give an indication whether the person is sick (e.g. having athlete's foot (Fußpilz in German)). In a shirt, the gas sensor 514 could give an indication about the smell level, which then could an indication for the health status.

FIG. 7 shows a schematic illustration of an order process of a product customized for a person according to the present invention. The process starts at step 701. In step 702 the design of the product is selected. As denoted by the reference numeral 703, different parameters can influence the design of the product. These parameters include for example the cultural context of the person for which the product is customized and manufactured, current trends, user preferences, location of the user and social data.

At step 704 a selection is made whether the product is a shoe or apparel.

If the product is a shoe, a sole is selected for the shoe at step 705. Selection of the sole is based on received sensor data obtained by at least one sensor integrated into a shoe which the person has previously worn during sports activities. It would also be possible that the person is able to select an existing sole material (like EVA, eTPU, ePEBA, TPU) and this sole is amended accordingly to the received sensor data. The parameters 706 influencing the sole selected at step 705 include for example whether the user typically performs outdoor or indoor sports, whether he puts strong loads on the heel, the level of desired waterproofness of the sole, its thickness and size.

For example, if the person is outdoors most of the time, an outdoor sole may be pre-selected. If the person is indoors most of the time, an indoor sole may be pre-selected. If the shoe is exposed to a lot of water a waterproof/water resistant sole may be pre-selected. If the person is a forest runner, a thin sole may be pre-selected as forest ground is flexible. If the person is a street runner, a thick sole may be pre-selected as resilience is required. If the person is a heel striker the heel of the sole may be stronger. If the exact size of the foot of the person is known the sole can be manufactured according to this size and is not limited to traditional, discrete shoe sizes.

At step 707 the bending of the sole, i.e. its general stiffness is selected. The parameters 709 influencing the bending of the shoe include for example whether the user is a forefoot or heel striker and whether he typically performs indoor or outdoor sports. The bending of the shoe may be adjusted by an appropriate placing of patches defined in step 708. Patch placement for the manufacturing of sports articles is for example described in applicant's patent application DE 10 2015 224 885.

In step 710 an upper is selected for the shoe. For example, a textile for the upper may be selected in step 710, either automatically based on the collected and evaluated sensor data or the user does a preselection by its own. The parameters 711 influencing the textile selected at step 710 include for example whether it is an upper for an outdoor or indoor shoe, the level of waterproofness of the upper, its thickness, size, pattern of textiles, material and the temperature at which the person usually performs sports activities. Temperature could include outside air temperature, body temperature or both.

For example, in the case of a running shoe, if the runner (i.e. person/user) is outdoors most of the time, an outdoor textile may be pre-selected. If the runner is indoors most of the time, and indoor textile may be pre-selected. If the shoe is exposed to a lot of water, waterproof/water resistance textile may be pre-selected. If the person is usually running in a high temperature environment, a breathing textile may be pre-selected. If the person is usually running in a low temperature environment, an insulating, warming material may be pre-selected. If the exact size of the foot of the person is known the upper can be manufactured according to this size and is not limited to traditional, discrete shoe sizes.

In step 712 one or more sensors are selected for the shoe. The selectable sensors may include for example accelerometers, gyroscopes, magnetometers, temperature sensors, piezo elements, pressure sensors, gas sensors and any combination thereof.

If at step 704 a determination was made that the customized product to be produced is an apparel (i.e. a product different than a shoe, like for example a shirt, jersey, trousers, blouse, cap, sock, leotard, leggings, etc.), the method proceeds to step 715 where one or more materials for the apparel are selected. The parameters 716 influencing the textile selected at step 715 include for example whether the apparel is for outdoor or indoor use, the level of waterproofness of the apparel, its thickness, size, pattern of textiles, material and the temperature at which the person usually performs sports activities. Temperature could include outside air temperature, body temperature or both. The parameters may also include whether the apparel is made to measure and any reinforcement used in the apparel.

In step 710 the customized product (i.e. a shoe from step 710 or an apparel from step 715) is finally produced according to the selections made in previous steps.

The method terminates in step 714.

An exemplary sensor insole 801 for measuring the pressure distribution under the foot is shown in FIGS. 8A, 8B and 8C. The insole 801 contains a capacitive matrix integrated into the insole for example by printing technologies. The capacitive matrix comprises alternating layers of conductive material and flexible/soft insulating material. When pressure is exerted on the flexible/soft material by the foot, the capacitance changes in the matrix proportional to the exerted pressure.

The layered arrangement of flexible/soft insulating material and conductive material is schematically shown in FIG. 8A in a sectional view. Under a top layer 802 of the insole 801 an upper insulation layer 803 is arranged. Under the upper insulation layer 803 the actual conductive matrix comprising four pairs of insulation layer and conductive printed layer is arranged. Thus, the sequence of layers of the conductive matrix from top to bottom is insulation layer 804, first conductive printed layer 805, insulation layer 806, second conductive printed layer 807, insulation layer 808, third conductive printed layer 809, insulation layer 810 and fourth conductive printed layer 811. Below the four pairs of layers of the conductive matrix a bottom insulation layer 812 is arranged above a final bottom layer of the insole. The foot 814 rests on the top layer 802 of the insole. The number and arrangement of layers shown in FIG. 8 is only an example and may vary in different applications. For example, the number of conductive layers may be more or less than those in FIG. 8.

FIG. 8B shows top views of each of the four conductive printed layers 805, 807, 809 and 811. The first conductive printed layer 805 and the fourth conductive printed layer 811 are ground layers, while the second conductive printed layer 807 and the third conductive printed layer 809 are the active layers. The second conductive printed layer 807 comprises a lateral-to-medial arrangement of conductive stripes. The third conductive printed layer 809 comprises a longitudinal arrangement of conductive stripes.

A variation of the capacitance can be measured at the points where the stripes of the second conductive printed layer 807 and the stripes of the third conductive printed layer 809 cross each other. Those points are arranged in the form of a matrix when the second conductive printed layer 807 and the third conductive printed layer 809 overlap in the insole 801. Thus, it is possible to measure capacitance, and thus pressure, at a plurality of points distributed over the entire insole.

FIG. 8C depicts a top view of the insole 801 with the integrated sensing area 815 provided by the conductive matrix as described above. Battery and electronics, e.g. a microcontroller, radio module and further sensors as described above can be arranged in the area 816, i.e. the area of the arch of the foot. The thickness of the area 816 may be 3-8 mm, preferably 5 mm. The electronics may be integrated, e.g. molded or releasably connected to the insole 801.

FIG. 9 shows a use case scenario for the sports shoe and method according to the present invention. A person (consumer) 901 wears a sensor-based sports shoe as described before. While the person is wearing the shoe, sensor data are obtained by at least one sensor integrated into the shoe. Besides using the sensor data to build a digital model of a new sports shoe customized for the person as described in detail herein, the sensor data may also be used for injury detection 902 which will be described in more detail with respect to FIG. 11.

A further application of the sensor data is a gait analysis. This gait analysis may be used to build a digital model for a new sports show customized for the person as described in detail herein. However, the gait analysis could also be presented to the user via a display on a mobile device like for example a smartphone, smartwatch, tablet computer, laptop computer, desktop computer or the like. To this end, in one exemplary embodiment the sensor data is transmitted from the sensor based shoe to a processing device performing the gait analysis, e.g. a smartphone, smartwatch, tablet computer, laptop computer, desktop computer or the like and transmitted from the processing device to the mobile device. The processing device and the mobile device could be the same device. Alternatively, the gait analysis is performed on the processor of the sensor-based shoe and transferred to the mobile device. Further alternatively, the sensor data may be preprocessed with the processor of the sensor-based shoe and the preprocessed data is transmitted to a processing device for performing the gait cycle analysis.

In general, transferring data between the sensor based shoe and a processing device or mobile device can be performed via Bluetooth, Bluetooth Low Energy, Wifi, NFC, a cellular network or the like. Also, it is possible to transmit the data via a wired connection like USB or a serial connection for example.

The gait analysis 903 could comprise the person's walking gait, the person's running gait or both as shown at reference numeral 904 in FIG. 9. As shown at reference numeral 905 in FIG. 9, the gait analysis could extend over the lifetime of the shoe or the person. In this case, long-term trends, deviations and changes of the person's gait cycle over the lifetime of the person can become visible in the lifetime gait analysis.

As shown at reference numeral 906, the sensor based shoe could be used in the context of a daily activity tracker as well. To this end, the sensor based shoe may transmit the gathered sensor data to a mobile device like a smartphone, smart-watch, tablet computer, multimedia player or the like. After processing the sensor data within the mobile device, the sensor data can then be presented to the user as a record of his/her daily activities on the mobile device. For example, the number of steps taken during a day could be extracted from the sensor data and presented to the person. Also, it is possible to compute the energy expenditure from appropriate sensor data and present the daily energy expenditure to the person. Further information that could be presented to the person in the context of a daily activity tracker include walking and/or running distance, walking and/or running time, ambient and/or body temperature, fastest speed of the day, etc.

In the context of a daily activity tracker service it is also possible to implement a weight tracker 909 based on the gathered sensor data. For example, the sensor data could include pressure information from a pressure sensor which could be used to determine the person's weight. It is then possible to present the daily weight to the person to provide an incentive for training. It is also possible that the person indicates a desired weight and that a training plan is generated based on the difference between the current weight and the desired weight.

Measuring the weight of a person is possible by using a piezo element or a pressure sensor. Using sensor data from these kind of sensors, it is possible to measure the weight of the person by measuring the force which is applied to the piezo element or the pressure sensor when the person stands, walks, or runs. During walking or running activities, the data from the piezo element or pressure sensor may be synchronized with data from an accelerometer to determine e.g. the exact point in time of ground contact.

Based on the weight it is possible to give the user health related messages (e.g. "train more", "your weight is higher than the last training", "train less as you are losing weight to fast"). Such messages could be based on a pre-entered body weight or based on a first measurement. The person could add weight ranges. Based on such ranges messages (see above) could be send to the user. Based on the determined weight a specific midsole and/or outsole with specific properties or materials could be amended or chosen. For example, the thickness of the midsole could be adapted to the weight of the user and the heavier the person is, the thicker the midsole could be to provide for sufficient cushioning. The outsole could be made more abrasion resistant if the person is rather heavy to counteract wear.

Reference numerals 907 and 908 in FIG. 9 represent the process 1007 of buying a new sports shoe customized for the person and of producing/manufacturing 908 the customized sports shoe based on a digital model, wherein the digital model is build based on received sensor data, wherein the received sensor data is obtained by at least one sensor integrated into the sensor based best shoe and, wherein the sensor data is obtained while the sensor based shoe is worn by the person during a sports activity as described in detail herein. To this end, the factory denoted by reference numeral 909 may request a gait analysis of the person. The gait analysis may be stored on a server (for example in a cloud) where it has been transmitted to from the sensor based shoe. Alternatively, the factory 909 may directly request the gait analysis from the processor/microcontroller in the sensor based shoe. Transferring the gait analysis between the sensor based shoe and the factory 909 can be performed via Bluetooth, Bluetooth Low Energy, Wifi, NFC, a cellular network or the like. Also, it is possible to transmit the data via a wired connection like USB or a serial connection for example. It is generally possible that the transfer takes place via intermediate devices such as computers, servers, routers, Wifi access points, DSL modems, Bluetooth beacons, NFC devices and the like.

The bottom rectangle of FIG. 9 shows a number of additional services which may be provided to the user 901 of the sensor based shoe. One such service is a visual run 910. In a visual run 910 the sensor data recorded by the at least one sensor in the sensor based shoe is applied to a human model of the person. Based thereon, the run can then be replayed to simulate body functions and to detect stress on the body. At the same time, a digital model of a new sports shoe customized for the person according to the present invention may be available. This digital model may be applied to the visual run simulate the impact on performance and the impact on the body of the person by the new customized shoe. GPS data recorded during the run may be used to show the person's geographic location on a map during the visual run. In addition, performance data like heart rate, pace, speed, cadence, etc. may be displayed.

A further service which may be provided to the person in the context of the present invention is a health report 911 which uses recorded sensor data to understand the performance and health of the person. Based on the sensor data gathered by the at least one sensor in the sensor based shoe a health report can be established. The health report may show for example whether the fitness level of the person has decreased, whether he started to slow down, abnormalities in heart rate, etc. If the health report indicates severe health problems, the person could be asked to contact a doctor. Alternatively, in such a case, a doctor (e.g. the family doctor) may be contacted automatically and the health report could be automatically transmitted to the doctor in electronic form. Generally, with the daily usage of the sensor based shoe, it is possible to detect stress 916 and to deliver recommendations for training.

Is also possible to provide a so-called locker outfitter service 912 to the user. For example, if the person forgot his/her sport clothes but has an urgent need for them, the locker outfitter service may deliver the needed sports clothes, in particular sports shoes, to the desired location (e.g. a gym) within a certain period of time (e.g. 8 hours). To this end, the sports clothes (for example shoes) may be produced (e.g. by using fully automated production techniques including 3D printing, placement of components by robots, knitting machines, etc.) based on a digital model stored in a database, server computer or cloud for example. The shoes may for example be produced in a shop or retail store near the person's current location to minimize delivery delay.

Another service is orthopedic sole design 913. In this case, the recorded sensor data is used to create an orthopedic sole design, i.e. a sole design considering the orthopedic properties and particularities of the person's foot. An orthopedic sole may be obtained according to the invention, i.e. sensor data obtained by at least one sensor integrated into the sensor based shoe may be received, wherein the sensor data is obtained while the sensor based shoe is worn by the person during a sports activity. A digital model of a new customized shoe including an orthopedic sole design based on the received sensor data is then build. Finally, the customized shoe including the orthopedic sole is manufacture based on the digital model. Alternatively, only an orthopedic sole is manufactured based on the sensor data or the digital model. For example, the sensor data or the digital model may be taken to an orthopedic shop (e.g. on a USB stick, CD rom, memory of a smartphone/table computer or transferred electronically via email, a cloud service, ftp, etc.) where an orthopedic sole is manufacture based on the sensor data or the digital model.

A further service which can be provided in the context of the present invention is shoe replacement prediction 914. According to this service, the age of the sports shoe is determined based on information stored e.g. in at least one sensor, a microcontroller or a memory in the sensor based shoe. When the sports shoe has reached a certain age, variations and changes in the shoe materials may negatively impact the gait cycle of the person. In this case, the person may be given a warning and a hint to buy new sports shoes which could be customized as described herein. Such a warning may be presented to the person on a display on a mobile device like a smartphone, smartwatch, tablet computer, multimedia player or the like. It is also possible to send an email, text message, text message service (SMS) or similar to the person. Also, the sports shoe could comprise an indicator (e.g. LED(s)) to indicate that the shoe has reached a certain age.

Another service which may be provided to the person in the context of the present invention is activity based shoe recommendation service 915. In this case recorded sensor data and optionally additional social information (e.g. from social networks) is used to detect daily activities including for example sports activities (e.g. street soccer, tennis, basketball, etc.), spare time activities, education/working times, etc. based on this information shoes for different sports and for daily use may be recommended to the user. For example if it is detected that a person is doing Cross Fit and running, the person could be given a recommendation to buy two different pairs of shoes optimized for the respective activities.

A further use case of a sensor based shoe is in the context of fitness tracking. During a run, the sensor based shoe may be in communication with a mobile device worn by the person like a smartphone, smartwatch, tablet computer, multimedia player or the like to transmit sensor data to the mobile device. The sensor data is processed on the mobile device and relevant information extracted from the sensor data is presented to the person in real-time on a display of the mobile device or via a speaker of the mobile device or via headphones which are connected wired or wireless to the mobile device. This information could for example include speed, pace, cadence and heart rate. If the mobile device is equipped with a positioning system module such as GPS, Glonass, Galileo or the like, the current position of the person during the run may be presented as well.

During such a run with the sensor based shoe it is also possible to present messages to the user as exemplarily shown in FIGS. 10A, 10B and 10C. Thus, in FIG. 10A the sensor data have shown that the person is overheating during the run. For example, the body temperature could have been above a certain threshold (e.g. 38° C.) during a certain period of time (e.g. 1 minute). If this is the case, a message could be presented to the person warning him/her about the overheating. The message could be accompanied by an optical or acoustical alarm or both. If the mobile device is equipped with a vibration device as is typically found in smartphones, a vibration alarm may be triggered as well alternatively or in addition. The body temperature may be measured as described with respect to FIGS. 3H and 3I, namely by temperature sensors integrated in the person's shoe(s) and/or running shirt.

Further exemplary messages which may be presented to the person are shown in FIGS. 10B and 10C. In the case of FIG. 10B, the person has reached 50 miles a week during a visual run and this information is immediately presented to him/her as an incentive. In the case of FIG. 10C, the person has completed 1000 km and this information is again immediately presented to him/her as an incentive. Further incentives which may be presented include for example energy expenditure (e.g. a certain number of calories consumed), number of steps taken, a certain level of speed reached, etc. The accomplished running distance of the person may be measured by means of a position sensor (like GPS, GLONASS, Galileo, etc.) which is used from the mobile device of the person (like his/her smartphone, tablet computer, smartwatch, activity tracking device, in another embodiment the position sensor (like GPS, GLONASS, Galileo, etc.) could also be included in the shoe(s). Or it may be extracted from other sensor data like an accelerometer and/or step counter, etc. (which are placed within the shoe(s)).

FIG. 11 illustrates details of injury detection 902 mentioned in FIG. 9. The process starts at step 1101. A step 1102 a person wearing a sensor based shoe according to the invention starts moving, e.g. running or walking. At step 1103 the gait cycle of the person is analyzed as described before. The gait cycle is then compared to a history 1104 of gait cycles in step 1105. The history of gait cycles may be stored in a database 1106 which may be located in a memory of the sensor based shoe. Alternatively, the database may be located on a person's personal device like a smartphone, tablet computer, digital media player or the like.

At step 1107 a decision is made based on the comparison of step 1105 whether the present gait is a normal gait or not. If this is the case, the process ends at step 1108. If the present gait is not a normal gait, rehabilitation mode is started at step 1109. In this mode, a rehabilitation advice may be presented to the person at step 1110. Such an advice may contain information of how the person may reach a normal gait again. The advice may be presented to the person on a display of a mobile device as mentioned before. Based on the stride pattern the stage of rehabilitation of the person may be estimated. An advice for certain exercises and the recommended length of running sessions may then be given for example. Based on the progress an advice could be given to visit a doctor again if there is no improvement.

The rehabilitation mode 1109 may also comprise an injury analysis 1111 which contains information about an injury causing a deviation from a normal gait. Such an analysis may be based on the gathered sensor data and may for example yield that the person has sprained ligaments. In case of a detected injury, a risk advice could be presented to the person at step 1112. The advice could indicate that proceeding further with the sports activity may lead to further serious injuries. The injury analysis may also be stored in the database 1106 for future reference and comparison.

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments of the system described with reference to the figures will so fully reveal the general nature of the invention that others can, by applying knowledge within the skill of the art, readily modify and/or adapt for various applications such specific embodiments, without undue experimentation, without departing from the general concept of the present invention.

While various embodiments of the present invention have been described above, they have been presented by way of example only, and not limitation. It should be apparent that adaptations and modifications are intended to be within the meaning and range of equivalents of the disclosed embodiments, based on the teaching and guidance presented herein. It therefore will be apparent to one skilled in the art that various changes in form and detail can be made to the embodiments disclosed herein without departing from the spirit and scope of the present invention. The elements of the embodiments presented above are not necessarily mutually exclusive, but may be interchanged to meet various needs as would be appreciated by one of skill in the art.

What is claimed is:

1. An article of sports apparel being customized for a person, comprising:
   the article of sports apparel, wherein the article of sports apparel is a first article of sports apparel manufactured based on a first digital model comprising a three-dimensional model and a functional description,
   wherein the first digital model is built based on received sensor data from a sensor embedded in a second article of sports apparel manufactured based on a second digital model, including gait cycle data, and updated in response to variation in the individual's gait cycle data over time,
   wherein the sensor data is obtained while the second article of sports apparel is worn by the person during a sports activity, and
   wherein a third article of sports apparel is manufactured based on a third digital model built based on the received sensor data.

2. The article of sports apparel according to claim 1, wherein the sensor data includes at least one parameter selected from the group of distance, speed, pace, heart rate, body temperature, weight, blood flow, energy expenditure, and geographic position.

3. The article of sports apparel according to claim 1, wherein the at least one sensor is selected from the group of a gyroscope, accelerometer, magnetometer, temperature sensor, pressure sensor, flex sensor, step counter, moisture sensor, and positioning system.

4. The article of sports apparel according to claim 1, wherein the sensor data includes sensor data from an accelerometer and a gyroscope.

5. The article of sports apparel according to claim 1, wherein the first article of sports apparel is a sports shoe and the other second article of sports apparel is another sports shoe.

6. The article of sports apparel according to claim 5, wherein the first digital model is based on at least one parameter selected from the group of the amount of time the person was running, the amount of time the person was walking, the amount of time the person was standing, the amount of time the person was sitting, the impact of forefoot strikes, the impact of midfoot strikes, the impact of heel strikes, pronation, stride distance, symmetry of the gait, and weight of the person.

7. The article of sports apparel according to claim 5, wherein the first article of apparel sports shoe includes a midsole, and wherein at least one selected from the group of the material, thickness, stiffness, insulation, and cushioning properties of the midsole is adapted based on the received sensor data.

8. The article of sports apparel according to claim 5, wherein the first article of apparel sports shoe includes an outsole, and wherein at least one selected from the group of material, thickness, stiffness, cushioning properties, abrasion resistance, and profile structure of the outsole is adapted based on the received sensor data.

9. The article of sports apparel according to claim 5, wherein the first article of apparel sports shoe includes an upper, and wherein at least one selected from the group of the material, thickness, stiffness, abrasion resistance, waterproofness, air permeability, insulation, and profile structure of the upper is adapted based on the received sensor data.

10. The article of sports apparel according to claim 1, further comprising:
    at least one sensor integrated into the first article of sports apparel which is capable to deliver sensor data for manufacturing a further article of sports apparel.

11. A method of manufacturing a first article of sports apparel, comprising the steps of:
    receiving sensor data obtained by at least one sensor integrated into a second article of sports apparel, wherein the sensor data is obtained while the second article of sports apparel is worn by a person during a sports activity;
    receiving social information about the person from a social network;
    building a first digital model comprising a three-dimensional model and a functional description of the first article of sports apparel based on the received sensor data and the social information;
    building a second digital model comprising a three-dimensional model and a functional description of a third article of sports apparel based on the received sensor data; and
    manufacturing the first and third articles of sports apparel based on the first and second digital models.

12. The method according to claim 11, wherein the method is performed in a retail store.

13. The method according to claim 11, wherein the sensor data includes at least one parameter selected from the group of distance, speed, pace, heart rate, body temperature, weight, blood flow, energy expenditure, and geographic position.

14. The method according to claim 11, wherein the at least one sensor is selected from the group of a gyroscope, accelerometer, magnetometer, temperature sensor, pressure sensor, flex sensor, step counter, moisture sensor, and positioning system.

15. The method according to claim 11, wherein the sensor data comprises sensor data from an accelerometer and a gyroscope.

16. The method according to claim 11, wherein the first article of sports apparel and the second article of sports apparel are both a sports shoe.

17. The method according to claim 15, wherein the first and second digital models are based at least in part on an analysis of the person's gait cycle by means of the received sensor data.

18. The method according to claim 16, wherein the first digital model is based at least on a parameter selected from the group of the amount of time the person was running, the amount of time the person was walking, the amount of time the person was standing, the amount of time the person was sitting, the impact of forefoot strikes, the impact of midfoot strikes, the impact of heel strikes, pronation, stride distance, symmetry of the gait, and weight of the person.

19. The method according to claim 16, wherein the first article of apparel sports shoe includes a midsole, and wherein one of the group selected from the material, thickness, stiffness, insulation, and cushioning properties of the midsole is adapted based on the received sensor data.

20. The method according to claim 16, wherein the first article of apparel sports shoe includes an outsole, and wherein one selected from the group of the material, thickness, stiffness, cushioning properties, abrasion resistance, and profile structure of the outsole is adapted based on the received sensor data.

21. The method according to claim 16, wherein the first article of apparel sports shoe includes an upper, and wherein one selected from the group of the material, thickness, stiffness, abrasion resistance, waterproofness, air permeability, insulation, and profile structure of the upper is adapted based on the received sensor data.

22. The method according to claim 11, wherein the first sports apparel includes at least one sensor which is capable to deliver sensor data for manufacturing the third sports apparel.

23. A first article of sports apparel made by a method of manufacturing, comprising the steps of:

receiving sensor data obtained by at least one sensor integrated into a second article of sports apparel, wherein the sensor data is obtained while the second article of sports apparel is worn by a person during a sports activity, and wherein the sensor data indicates negative impact of a gait cycle of the person;

alerting the person that the second article of sports apparel should be replaced in response to the negative impact of a gait cycle;

building a first digital model comprising a three-dimensional model and a functional description of the first article of sports apparel based on the received sensor data;

manufacturing the first article of sports apparel based on the first digital model, wherein the method is performed in a retail store;

building a second digital model based on the received sensor data; and manufacturing a third article of sports apparel based on the second digital model.

* * * * *